(12) United States Patent
Hill

(10) Patent No.: US 7,145,663 B2
(45) Date of Patent: Dec. 5, 2006

(54) CATOPTRIC IMAGING SYSTEMS COMPRISING PELLICLE AND/OR APERTURE-ARRAY BEAM-SPLITTERS AND NON-ADAPTIVE AND/OR ADAPTIVE CATOPTRIC SURFACES

(75) Inventor: Henry Allen Hill, Tucson, AZ (US)

(73) Assignee: Zetetic Institute, Tucson, AZ (US)

( * ) Notice: Subject to any disclaimer, the term of this patent is extended or adjusted under 35 U.S.C. 154(b) by 15 days.

(21) Appl. No.: 11/229,314

(22) Filed: Sep. 16, 2005

(65) Prior Publication Data

US 2006/0066873 A1 Mar. 30, 2006

Related U.S. Application Data

(60) Provisional application No. 60/611,564, filed on Sep. 20, 2004.

(51) Int. Cl.
*G01B 9/02* (2006.01)

(52) U.S. Cl. .................................................. 356/512

(58) Field of Classification Search ............... 356/450, 356/489, 495, 511, 512, 513, 514, 515, 521; 378/36; 250/372
See application file for complete search history.

(56) References Cited

U.S. PATENT DOCUMENTS

| | | | |
|---|---|---|---|
| 3,628,027 A | 12/1971 | Brauss |
| 3,748,015 A | 7/1973 | Offner |
| 4,011,011 A | 3/1977 | Hemstreet et al. |
| 4,226,501 A | 10/1980 | Shafer |
| 4,272,684 A | 6/1981 | Seachman |
| 4,408,884 A | 10/1983 | Kleinknecht et al. |
| 4,672,196 A | 6/1987 | Canino |
| 4,685,803 A | 8/1987 | Sommargren |
| 4,733,967 A | 3/1988 | Sommargren |
| 5,220,403 A | 6/1993 | Batchelder et al. |
| 5,241,423 A | 8/1993 | Chiu et al. |
| 5,327,223 A | 7/1994 | Korth |
| 5,384,639 A | 1/1995 | Wickramasinghe |
| 5,392,118 A | 2/1995 | Wickramasinghe |
| 5,485,317 A | 1/1996 | Perissinotto |
| 5,602,643 A | 2/1997 | Barrett |
| 5,614,763 A | 3/1997 | Womack |
| 5,633,972 A | 5/1997 | Walt et al. |
| 5,659,420 A | 8/1997 | Wakai |
| 5,699,201 A | 12/1997 | Lee |
| 5,757,493 A | 5/1998 | Vaknerkhove |
| 5,760,901 A | 6/1998 | Hill |

(Continued)

OTHER PUBLICATIONS

U.S. Appl. No. 60/442,858, filed Jan. 27, 2003, Hill.

(Continued)

*Primary Examiner*—Samuel A. Turner
(74) *Attorney, Agent, or Firm*—Wilmer Cutler Pickering Hale and Dorr LLP

(57) ABSTRACT

An interferometry system including: a first imaging system that directs a measurement beam at an object to produce a return measurement beam from the object, that directs the return measurement beam onto an image plane, and that delivers a reference beam to the image plane; and a beam combining element in the image plane, said beam combining element comprising a first layer containing an array of sagittal slits and a second layer containing an array of tangential slits, wherein each slit of the array of sagittal slits is aligned with a corresponding different slit of the array of tangential slits, wherein the beam combining element combines the return measurement beam with the reference beam to produce an array of interference beams.

31 Claims, 18 Drawing Sheets

U.S. PATENT DOCUMENTS

| | | | |
|---|---|---|---|
| 5,828,455 A | 10/1998 | Smitth | |
| 5,894,195 A | 4/1999 | McDermott | |
| 5,915,048 A | 6/1999 | Hill et al. | |
| 5,923,423 A | 7/1999 | Sawatari et al. | |
| 6,011,654 A | 1/2000 | Schweizer et al. | |
| 6,018,391 A | 1/2000 | Yoshida | |
| 6,052,231 A | 4/2000 | Rosenbluth | |
| 6,091,496 A | 7/2000 | Hill | |
| 6,124,931 A | 9/2000 | Hill | |
| 6,271,923 B1 | 8/2001 | Hill | |
| 6,330,065 B1 | 12/2001 | Hill | |
| 6,445,453 B1 | 9/2002 | Hill | |
| 6,447,122 B1 | 9/2002 | Kobayashi et al. | |
| 6,469,788 B1 | 10/2002 | Boyd et al. | |
| 6,480,285 B1 | 11/2002 | Hill | |
| 6,552,805 B1 | 4/2003 | Hill | |
| 6,552,852 B1 | 4/2003 | Hill | |
| 6,597,721 B1 | 7/2003 | Hutchinson et al. | |
| 6,606,159 B1 | 8/2003 | Hill | |
| 6,667,809 B1 | 12/2003 | Hill | |
| 6,707,561 B1 | 3/2004 | Budach et al. | |
| 6,714,349 B1 | 3/2004 | Nam | |
| 6,717,736 B1 | 4/2004 | Hill | |
| 6,753,968 B1 | 6/2004 | Hill | |
| 6,771,374 B1 | 8/2004 | Rangarajan et al. | |
| 6,775,009 B1 | 8/2004 | Hill | |
| 6,806,959 B1 | 10/2004 | Tukker | |
| 6,847,029 B1 | 1/2005 | Hill | |
| 6,847,452 B1 | 1/2005 | Hill | |
| 2002/0074493 A1 | 6/2002 | Hill | |
| 2002/0131179 A1 | 9/2002 | Hill | |
| 2003/0174992 A1 | 9/2003 | Levene | |
| 2004/0201852 A1 | 10/2004 | Hill | |
| 2004/0201853 A1 | 10/2004 | Hill | |
| 2004/0201854 A1 | 10/2004 | Hill | |
| 2004/0201855 A1 | 10/2004 | Hill | |
| 2004/0202426 A1 | 10/2004 | Hill | |
| 2004/0227950 A1 | 11/2004 | Hill | |
| 2004/0227951 A1 | 11/2004 | Hill | |
| 2004/0228008 A1 | 11/2004 | Hill | |
| 2004/0246486 A1 | 12/2004 | Hill | |
| 2004/0257577 A1 | 12/2004 | Hill | |
| 2005/0036149 A1 | 2/2005 | Hill | |
| 2005/0111006 A1 | 5/2005 | Hill | |
| 2005/0111007 A1 | 5/2005 | Hill | |

OTHER PUBLICATIONS

U.S. Appl. No. 60/444,707, filed Feb. 4, 2003, Hill.
U.S. Appl. No. 60/448,360, filed Feb. 19, 2003, Hill.
U.S. Appl. No. 60/485,255, filed Jul. 7, 2003, Hill.
U.S. Appl. No. 60/507,675, filed Oct. 1, 2003, Hill.
U.S. Appl. No. 60/573,196, filed May 21, 2004, Hill.
U.S. Appl. No. 60/568,774, filed May 6, 2004, Hill.
U.S. Appl. No. 60/485,507, filed Jul. 7, 2003, Hill.
U.S. Appl. No. 60/459,425, filed Apr. 11, 2003, Hill.
U.S. Appl. No. 60/445,739, filed Feb. 7, 2003, Hill.
U.S. Appl. No. 60/442,982, filed Jan. 29, 2003, Hill.
U.S. Appl. No. 60/448,250, filed Feb. 19, 2003, Hill.
U.S. Appl. No. 60/460,129, filed Apr. 3, 2003, Hill.
U.S. Appl. No. 60/506,715, filed Sep. 26, 2003, Hill.
U.S. Appl. No. 60/571,967, filed May 18, 2004, Hill.
U.S. Appl. No. 60/569,807, filed May 11, 2004, Hill.
U.S. Appl. No. 60/501,666, filed Sep. 10, 2003, Hill.
U.S. Appl. No. 60/459,493, filed Apr. 1, 2003, Hill.
U.S. Appl. No. 60/447,254, filed Feb. 13, 2003, Hill.
U.S. Appl. No. 60/443,980, filed Jan. 31, 2003, Hill.

CATOPTRIC IMAGING SYSTEMS COMPRISING PELLICLE AND/OR APERTURE-ARRAY BEAM-SPLITTERS AND NON-ADAPTIVE AND/OR ADAPTIVE CATOPTRIC SURFACES

This application also claims the benefit of U.S. Provisional Application No. 60/611,564, filed Sep. 20, 2004, incorporated herein by reference.

TECHNICAL FIELD

This invention relates to interferometric imaging and metrology systems operating in the IR to EUV such as used in fabrication and inspection of wafers, integrated circuits, and reticle masks.

RELATED APPLICATIONS

The following applications are related to the present application: U.S. Pat. No. 6,552,852, issued Apr. 22, 2003 and entitled "Catoptric and Catadioptric Imaging Systems," (ZI-38); U.S. Ser. No. 60/447,254, filed Feb. 13, 2003, and U.S. Ser. No. 10/778,371, filed Feb. 13, 2004, both of which are entitled "Transverse Differential Interferometric Confocal Microscopy," (ZI-40); U.S. Ser. No. 60/448,360, filed Feb. 19, 2003, and U.S. Ser. No. 10/782,057, filed Feb. 19, 2004, both of which are entitled "Longitudinal Differential Interferometric Confocal Microscopy For Surface Profiling," (ZI-41); U.S. Ser. No. 60/448,250, filed Feb. 19, 2003, and U.S. Ser. No. 10/782,058, filed Feb. 19, 2004, both of which are entitled "Method And Apparatus For Dark Field Interferometric Confocal Microscopy," (ZI-42); U.S. Pat. No. 6,717,736, issued Apr. 6, 2004, entitled "Catoptric and Catadioptric Imaging Systems," (ZI-43); U.S. Ser. No. 60/442,892, filed Jan. 28, 2003 and U.S. Ser. No. 10/765,229, filed Jan. 27, 2004, both of which are entitled "Interferometric Confocal Microscopy Incorporating Pinhole Array Beam-Splitter," (ZI-45); U.S. Ser. No. 60/459,493, filed Apr. 1, 2003, and U.S. Ser. No. 10/816,201, filed Apr. 1, 2004, both of which are entitled "Method for Manufacture of Catadioptric Lens System," (ZI-48); U.S. Ser. No. 60/459,425, filed Apr. 1, 2003, entitled "Apparatus And Method For Joint Measurement Of Fields Of Scattered/Reflected Orthogonally Polarized Beams By An Object In Interferometry," and U.S. Ser. No. 10/816,180, filed Apr. 1, 2004, entitled "Apparatus And Method For Joint Measurement Of Fields Of Scattered/Reflected Or Transmitted Orthogonally Polarized Beams By An Object In Interferometry," (ZI-50); U.S. Ser. No. 60/485,507, filed Jul. 7, 2003, and U.S. Ser. No. 10/886,010, filed Jul. 7, 2004, both of which are entitled "Apparatus And Method For High Speed Scan For Sub-Wavelength Defects And Artifacts In Semiconductor Metrology," (ZI-52); U.S. Ser. No. 60/485,255, filed Jul. 7, 2003, and U.S. Ser. No. 10/886,157, filed Jul. 7, 2004, both of which are entitled "Apparatus and Method for Ellipsometric Measurements With High Spatial Resolution," (ZI-53); U.S. Ser. No. 60/501,666, filed Sep. 10, 2003, and U.S. Ser. No. 10/938,408, filed Sep. 10, 2004, both of which are entitled "Catoptric and Catadioptric Imaging Systems with Adaptive Catoptric Surfaces," (ZI-54); U.S. Ser. No. 60/506,715, filed Sep. 26, 2003, entitled "Catoptric and Catadioptric Imaging Systems Comprising Pellicle Beam-Splitters and Non-Adaptive and Adaptive Catoptric Surfaces," and U.S. Ser. No. 10/948,959, filed Sep. 24, 2004, entitled "Catoptric and Catadioptric Imaging Systems with Pellicle and Aperture-Array Beam-Splitters and Non-Adaptive and Adaptive Catoptric Surfaces," (ZI-56); and U.S. Ser. No. 60/602,046, filed Aug. 16, 2004, and U.S. Ser. No. 11/204,758, filed Aug. 16, 2005, both of which are entitled "Apparatus and Method for Joint and Time Delayed Measurements of Components of Conjugated Quadratures of Fields of Reflected/Scattered Beams by an Object in Interferometry," (ZI-57), all of which are incorporated herein by reference.

BACKGROUND OF THE INVENTION

A number of different applications of catadioptric imaging systems for far-field and near-field interferometric confocal microscopy have been described such as in various of the commonly owned U.S. Patents, U.S. Provisional Applications, U.S, Non-Provisional Applications listed above.

In some of the catadioptric imaging systems that are described in those patents and patent applications, conjugate images of pinhole arrays in or on a substrate, pinhole array beam combining beam-splitters, and/or arrays of detector pixels are located in two-dimensional planes with off-axis aberrations compensated to extend the field of view for diffraction limited imaging by the use of concentric dispersive elements.

In contrast, at least some of the embodiments described herein reduce the effects of off-axis aberrations by the use of conjugate arrays of orthogonal slits located on the sagittal and tangential surfaces in either the object space to generate a diffraction limited spot on a measurement object and/or in the image space of catoptric imaging systems to obtain diffraction limited information about a spot on a measurement object.

Also in certain of the applications of catadioptric imaging systems that are described in the above-identified patents and patent applications, a beam-splitter is incorporated in generating an image of an object with zero optical aberrations for a measurement object located on the optic axis of the imaging system. The beam-splitter is located at an interface between relatively thick optical elements of the catadioptric imaging systems. The optical elements contribute as well as compensate off-axis aberrations and cause a significant portion of optical paths in the catadioptric imaging systems to comprise a refractive medium such as fused silica or $CaF_2$.

In contrast, at least some of the embodiments described herein involve use of a thin beam-splitter in catoptric imaging systems to generate an image of a measurement object with zero or substantially zero optical aberrations for an object located on the optic axis of the imaging system configured for operation in the IR to EUV. The use of the thin beam-splitter reduces the magnitude of both the off-axis and on-axis aberrations that may or may not require subsequent compensation, increases the field of view that may be used, and reduces the optical path length in a transmitting refractive medium which is particularly important when working in either the IR to the EUV.

Also in certain of the applications of catadioptric imaging systems that are described in the above-identified patents and patent applications, tight tolerances are generally placed on the manufacture of optical elements. In addition to the tolerances normally encountered in designing a diffraction limited imaging system, there are additional tolerances imposed in interferometric confocal and non-confocal microscopy applications. The additional tolerances are for example on surfaces of certain elements with respect to radii of curvature and on relative locations of centers of curvature of the surfaces of the certain elements.

The additional tolerances lead to improved performance of a catoptric imaging system, e.g., with respect to increasing the average intensity of desired images by a factor of approximately 2 and reduced intensity of spurious beams by one or more order of magnitudes, and in addition make it possible to realize interferometric reduction of background fields. The interferometric reduction of background fields leads to a reduction of statistical errors. The increase in intensity of desired images and the reduction of statistical errors lead to an increase in signal-to-noise ratios and to a concomitant increase in throughput of a metrology tool using the catoptric imaging system. The interferometric reduction of background fields further leads to a reduction of systematic errors. A consequence of the reduction of systematic errors is a reduction of the computational task required to invert arrays of measured interference signal values to a multi-dimensional image of a measurement object.

At least some of the above-identified U.S. Patents, U.S. Patent Applications, and U.S. Provisional Patent Applications further teach the use of adaptive catoptric surfaces in a catoptric or catadioptric imaging system. The use of adaptive catoptric surfaces in a catoptric imaging system makes it possible to relax tolerances on the surface figures of elements, to relax tolerances on locations of surfaces of the elements in the catoptric imaging system, and to compensate for certain optical aberrations such as may be introduced by the pellicle or aperture-array beam-splitter. The factor by which the tolerances may be relaxed on the surface figures is of the order of 5 for certain of the elements. The use of adaptive catoptric surfaces in a catoptric imaging system further makes it possible to introduce a vertical or lateral scan of a measurement object or substrate being imaged at slew rates higher then possible and/or practical when the vertical or lateral scan must otherwise be introduced either by translations of an entire catoptric imaging system and associated optics and detector systems or translations of the measurement object or substrate, e.g., a 300 mm wafer, and the measurement object or substrate support system.

Certain of the above-identified cited U.S. Patents, U.S. Patent Applications, and U.S. Provisional Patent Applications further teach the replacement of a beam combining beam-splitter in an interferometric imaging system with an interface comprising a thin fluorescent layer or array of thin fluorescent spots.

The cited U.S. Patents, U.S. Patent Applications, and U.S. Provisional Patent Applications also teach the use of an N-dimensional bi- and quad-homodyne detection methods.

The use of multi-element adaptive catoptric surfaces in catoptric imaging systems also makes it possible to compensate for optical aberrations such as may be introduced by a pellicle or aperture-array beam-splitter or such as introduced when imaging a plane section of a substrate wherein one or more plane refracting surfaces are located for example in the object space of the catoptric imaging system near and in front of the plane section of the substrate. The compensation of the optical aberrations corresponds to the conversion of one or more spherical catoptric surfaces to one or more aspherical catoptric surfaces.

As described herein, the replacement of a beam combining beam-splitter in interferometric imaging system with a beam combining thin fluorescent layer or interface or with an array of thin fluorescent spots for operation in the UV to EUV impacts on the performance specifications required of optical elements of the interferometric imaging system and/ or detector that follow the beam combining function to achieve a certain end use performance. The thin fluorescent layer or array of fluorescent spots, e.g., lumogen, absorbs light at one wavelength, e.g., the EUV, and emits light at a longer wave length, e.g., in the visible, to generate an optical interference signal. The optical interference signal is subsequently converted to an electrical interference signal when the longer wavelength light is detected by a detector. Thus, there is a concomitant reduction in the required performance specifications of the optical elements because the optical elements serve only to transmit beams and generate optical images at the longer wavelength instead of at the shorter wavelength beam in the UV to EUV. The shorter wavelength beam that is absorbed is a mixed beam which comprises a measurement beam component and a reference beam component in the same polarization state.

In the case where a beam-splitter is used for the beam combining function, the measurement beam component and the reference beam component of the combined beam may have subsequent to the beam-splitter different paths in the optical elements which introduce the possibility of non-common path phase errors. The possibility of non-common path phase errors is not present when a thin fluorescent layer or array of fluorescent spots serves the beam combining function.

When the shorter wavelength beam has a wavelength in the UV to EUV and a thin fluorescent layer or array of fluorescent spots serves the beam combining function, there is a significant change in the required performance of the detector because it has to serve to only detect the longer wavelength optical beam instead of the shorter wavelength mixed beam. The advantage of at least some of the embodiments described herein with respect to the reduction on the required performance specifications of the optical elements and the detector is valid for measurement and reference beams comprising UV to EUV wavelengths.

The implementation of the N-dimensional bi- and quad-homodyne detection methods make it possible to extend the advantages of the bi- and quad-homodyne detection methods for measuring conjugated quadratures of fields jointly to homodyne methods for measuring conjugated quadratures of fields when measuring jointly N different properties of the fields.

SUMMARY OF THE INVENTION

Catoptric IR to EUV imaging systems configured with large numerical apertures are described that reduce the effects of off-axis optical aberrations for generation of enhanced fields of view. The catoptric IR to EUV imaging systems comprise a thin beam-splitter, thin with respect to generation of optical aberrations and/or internal absorption, and/or an aperture-array beam-splitter. The effects of off-axis aberrations are reduced in certain embodiments by complimentary arrays of orthogonal slits located on the sagittal and tangential surfaces in either the object space and/or in the image space of the catoptric imaging systems. The catoptric imaging systems in the certain embodiments may be used to generate a diffraction limited spot on a measurement object or used to obtain diffraction limited information about a spot on a measurement object. The catoptric surfaces of the catoptric imaging systems may comprise adaptive catoptric surfaces wherein each of the one or more adaptive catoptric surfaces is generated by an array of reflecting elements. The thin beam-splitter may be a pellicle beam-splitter comprising a self supporting stack of one or more thin layers of refractive media and the aperture-array beam-splitter may comprise a thin self supporting reflective stack of one or more refractive layers with an array of transmitting apertures or an array or grid of conducting wires wherein the size of the apertures is generally larger than the wavelength of an optical beam being focused by the imaging systems.

In comparison to certain catoptric imaging systems that comprise a non-thin beam-splitter, the use of a thin beam-splitter reduces the magnitude of both off-axis and on-axis aberrations and further reduces the optical path length of measurement and/or reference beams in a dispersive or refractive medium which is particularly important when working in the UV to EUV. The catoptric imaging systems may be configured to have a large working distance, e.g., 6 mm. In addition, the catoptric imaging systems may be employed in interferometric or non-interferometric imaging systems operating in a reflecting mode to measure properties of fields reflected/scattered by a measurement object or substrate or in a transmission mode to measure properties of fields transmitted/scattered by a measurement object or substrate, e.g., a reticle mask.

The positions and orientations of the reflecting elements of the one or more adaptive surfaces are controlled by transducers and a servo control system. The use of multi-element adaptive catoptric surfaces makes it possible to relax tolerances on the surface figures and locations of surfaces of the reflecting elements, makes it possible to introduce a mode of operation such that the image of a plane section of a measurement object is fixed in an image plane for a short period of time that covers the duration of a beam pulse generating the image although the plane section of the measurement object is moving in the object space at a high slew rate, makes it possible to introduce modes of operation that increases the speed at which lateral and vertical scans of a substrate may be implemented, makes it possible to introduce modes of operation that increase the signal-to-noise ratios for image information generated with the catoptric imaging systems, and makes it possible to operate in either a differential or non-differential interferometric mode with the option of switching rapidly between either of the differential or the non-differential modes of operation.

In general, in one aspect, the invention features an interferometry system including: a first imaging system that directs a measurement beam at an object to produce a return measurement beam from the object, that directs the return measurement beam onto an image plane, and that delivers a reference beam to the image plane; and a beam combining element in the image plane, said beam combining element comprising a first layer containing an array of sagittal slits and a second layer containing an array of tangential slits, wherein each slit of the array of sagittal slits is aligned with a corresponding different slit of the array of tangential slits, wherein the beam combining element combines the return measurement beam with the reference beam to produce an array of interference beams.

Other embodiments include one or more of the following features. The interferometry system further includes: a detector array; and a second imaging system that directs the array of interference beams from the beam combining element onto the detector array. The measurement beam is characterized by a wavelength $\lambda$, the first layer is made of a first absorbing material that absorbs at wavelength $\lambda$, and the second layer is made of a second absorbing material that absorbs at wavelength $\lambda$. The first and second absorbing materials are the same. The first layer is a planar-shaped layer and the second layer is a concave-shaped layer. The beam combining element further includes a third layer sandwiched between the first and second layers. The third layer is transmissive at wavelength $\lambda$. Alternatively, the third layer is absorbing at wavelength $\lambda$ and it includes an array of apertures each of which is aligned with a corresponding different one of the slits of the sagittal array of slits. The first imaging system is characterized by a sagittal imaging surface and a tangential imaging surface and wherein the first layer conforms to the sagittal imaging surface and the second layer conforms to the tangential imaging surface. The first imaging system is a catoptric imaging system. The first imaging system is characterized by an optical axis and the slits of the sagittal array of slits are aligned along radial directions relative to the optical axis and the slits of the tangential array of slits are aligned along azimuthal directions relative to the optical axis. The lengths of the slits of the sagittal array of slits increase as a function of the distance of the slit from the optical axis. The lengths of the slits of the tangential array of slits increase as a function of the distance of the slit from the optical axis. The slits of the sagittal array of slits are v-shaped grooves. The slits of the tangential array of slits are v-shaped grooves. The slits of the sagittal array of slits are filled with a fluorescent material. The fluorescent material is lumogen. The fluorescent material is sensitive to UV, VUV or EUV. The fluorescent material is responsive to radiation at a first wavelength and emits radiation at a second wavelength, wherein the first and second wavelengths are different. The second wavelength is longer than the first wavelength. The fluorescent material is responsive to radiation in the UV, VUV or EUV region and the second wavelength is in the visible region. The interferometry system further includes: a detector array that is responsive to radiation at the second wavelength; and a second imaging system that directs the array of interference beams from the beam combining element onto the detector array.

Other embodiments also include one or more of the following features. The first imaging system includes: a beam splitting element positioned to receive the return measurement beam from the object and separate the return measurement beam into a transmitted portion and a reflected portion; and a reflecting surface positioned to receive one of the transmitted portion and the reflected portion from the beam splitting element and focus that received portion onto the image plane via the beam splitter. The first imaging system includes an array of independently positionable reflecting elements forming the reflecting surface. The reflecting surface is a Fresnel reflecting surface. The reflecting surface is positioned to receive the transmitted portion of the measurement beam and reflect the transmitted portion of the measurement beam back to the beam splitter, and wherein the beam splitter is positioned to reflect rays received from the reflecting surface toward the image plane. The interferometry system further includes a beam splitting element including a first layer containing an array of sagittal slits and a second layer containing an array of tangential slits, wherein each slit of the array of sagittal slits of the beam splitting element is aligned with a corresponding different slit of the array of tangential slits of the beam splitting element, wherein the beam combining element receives a source beam and generates therefrom an array of measurement beam components, said array of measurement beam components making up the measurement beam.

In general, in another aspect the invention features an interferometry system including: a first imaging system that directs a measurement beam at an object to produce a return measurement beam from the object, that directs the return measurement beam onto an image plane, and that delivers a reference beam to the image plane; and a beam combining element in the image plane, said beam combining element comprising an array of apertures that are configured and arranged to combine the return measurement beam with the reference beam to produce an array of interference beams containing diffraction limited information.

In general, in yet another aspect, the invention features an interferometry system including: a beam splitting element comprising a first layer containing an array of sagittal slits and a second layer containing an array of tangential slits, wherein each slit of the array of sagittal slits is aligned with a corresponding different slit of the array of tangential slits, wherein the beam splitting element receives a source beam and generates therefrom an array of measurement beams; an imaging system that directs the array of measurement beams at an object to produce an array of return measurement beams from the object, that directs the array of return measurement beams onto an image plane, and that delivers a reference beam to the image plane; and a beam combining element in the image plane that combines the array of return measurement beams with the reference beam to produce an array of interference beams.

An advantage of at least one embodiment of the present invention is the reduction of effects of off axis optical aberrations introduced by different elements of a catoptric imaging system.

Another advantage of at least one embodiment of the present invention is the reduction of effects of on-axis optical aberrations introduced by different elements of a catoptric imaging system.

Another advantage of at least one embodiment of the present invention is an enhanced field of view of a catoptric imaging system that is diffraction limited with respect to information obtained.

Another advantage of at least one embodiment of the present invention is the generation of detected images with catoptric imaging systems that have a large numerical aperture.

Another advantage of at least one embodiment of the present invention is a reduction of optical path length for reference and/or measurement beams in a refractive medium in an interferometric imaging system.

Another advantage of at least one embodiment of the present invention is the extension of the range of wavelengths from the IR to the EUV that may be used in a catoptric imaging system.

Another advantage of at least one embodiment of the present invention is that a catoptric imaging system may be employed in interferometric or non-interferometric imaging systems.

Another advantage of at least one embodiment of the present invention is that a catoptric imaging system may be employed in an interferometric or non-interferometric imaging system operating in a reflecting mode to measure properties of fields reflected/scattered by a substrate.

Another advantage of at least one embodiment of the present invention is that a catoptric imaging system may be employed in an interferometric or non-interferometric imaging system operating in a transmitting mode to measure properties of fields transmitted/scattered by a substrate.

Another advantage of at least one embodiment of the present invention is that use of multi-element adaptive catoptric surfaces makes it possible to introduce a mode of operation such that the image of a plane section of an object is fixed in an image plane for a short period of time that covers the duration of a beam pulse generating the image although the plane section of the object is moving in the object space at either a low or high slew rate.

Another advantage of at least one embodiment of the present invention is that a catoptric imaging system may be used with a large working distance.

Another advantage of at least one embodiment of the present invention is that a catoptric imaging system may be used to generate a diffraction limited spot on a measurement object.

Another advantage of at least one embodiment of the present invention is the acquisition of diffraction limited information of plane sections embedded in substrate.

Another advantage of at least one embodiment of the present invention is high speed vertical scans with the acquisition of diffraction limited information of plane sections embedded in substrate.

Another advantage of at least one embodiment of the present invention is high speed lateral scans with the acquisition of diffraction limited information of a plane section embedded in substrate.

Another advantage of at least one embodiment of the present invention is a high speed approach to and acquisition of a substrate surface.

Another advantage of at least one embodiment of the present invention is lateral differential interferometric measurements of a plane section embedded in substrate.

Another advantage of at least one embodiment of the present invention is differential measurements of spatial Fourier components of a plane section embedded in a substrate.

Another advantage of at least one embodiment of the present invention is high speed lateral differential interferometric scans of an embedded plane section of a substrate.

Another advantage of at least one embodiment of the present invention is the use of high speed N-dimensional bi- and quad-homodyne detection methods.

Another advantage of at least one embodiment of the present invention is a phase modulating mode of operation.

Another advantage of at least one embodiment of the present invention is an optical switching mode of operation.

Another advantage of at least one embodiment of the present invention is the option to use an array of thin fluorescent spots as a beam combining beam-splitter in an interferometer system to increase the resolution of the imaging system used in the interferometer system and/or to reduce the magnitude of the contribution of background to a measured electrical interference signal.

DETAILED DESCRIPTION

Figure 1A:
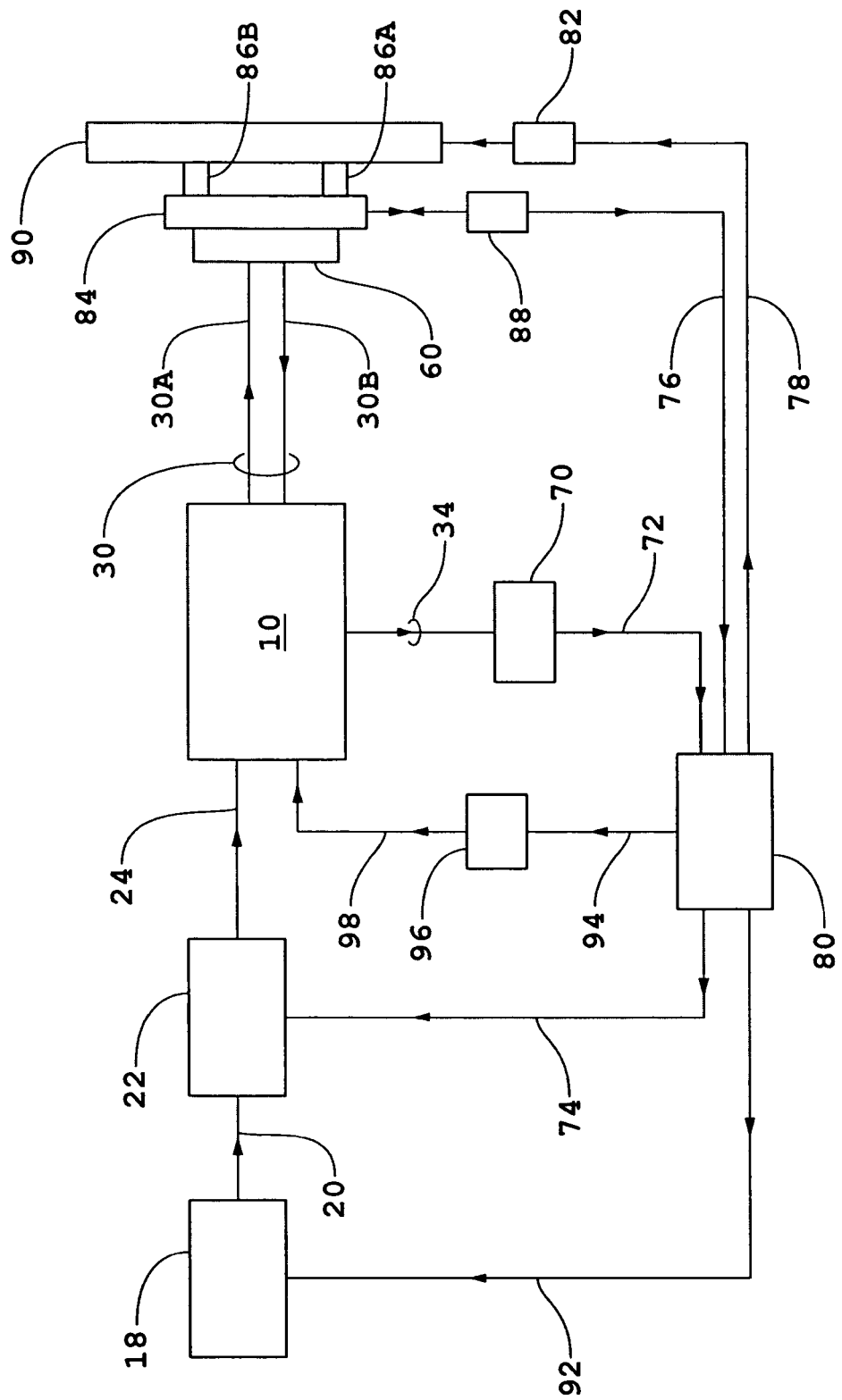
FIG. 1a is a schematic diagram of an interferometric system operating in a reflecting mode.

A general description of embodiments incorporating the present invention will first be given for interferometer systems wherein either a N-dimensional bi- or quad-homodyne detection method is used where N is an integer. Referring to FIG. 1a, an interferometer system is shown diagrammatically comprising an interferometer 10, a source 18, a beam-conditioner 22, a detector 70, an electronic processor and controller 80, and a measurement object shown as substrate 60. Source 18 generates input beam 20. The interferometer system shown in FIG. 1a is for the case of an imaging system operating in a reflecting mode to measure properties of fields reflected/scattered by substrate 60. For the case of operation in a transmission mode, a portion of beam 24 split off as a measurement beam is incident on substrate 60 from the backside of substrate 60 such as shown diagrammatically in FIG. 2a. Source 18 is preferably a pulsed source that generates beam 20 with a single frequency component. Beam 20 is incident on and exits beam-conditioner 22 as input beam 24 that has the one or more frequency components.

Alternatively, source 18 and beam-conditioner 22 may generate beam 24 with two or more frequency components that may have different polarization states wherein input beam 24 has one or more frequency components for each of the different polarization states. The different frequency components of the measurement beam components of input beam 24 are coextensive in space, the different frequency components of the reference beam components of input beam 24 are coextensive in space, and the different frequency components of both the reference and measurement beam components have the same temporal window function. In addition, the different frequency components of the reference and measurement beam components of input beam 24 may be coextensive in space. Further description of source 18 and beam-conditioner 22 is the same as the corresponding description in commonly owned U.S. Provisional Patent Application No. 60/602,046 (ZI-57) and U.S. patent application filed Aug. 16, 2004 (ZI-57) wherein each is entitled "Apparatus and Method for Joint And Time Delayed Measurements of Components of Conjugated Quadratures of Fields of Reflected/Scattered and Transmitted/Scattered Beams by an Object in Interferometry" and both are by Henry A. Hill, the contents of which are herein incorporated in their entirety by reference.

In the various embodiments of the present invention operating in either the reflecting or transmitting mode and configured for interferometric metrology, components of conjugated quadratures of fields reflected/scattered or transmitted/scattered, respectively, are measured either jointly or non-jointly. For each of the embodiments configured for interferometric metrology, non-interferometric variants are obtained by the omission of the reference beam wherein only the intensity of fields reflected/scattered or transmitted/scattered, respectively, are measured.

Interferometer 10 comprises a catoptric imaging system that may have one or more adaptive reflecting surfaces. The shapes of the one or more adaptive reflecting surfaces are controlled by a signal 98 from servo controller 96 according to error signal 94 from electronic processor and controller 80.

Reference and measurement beams are generated in either beam-conditioner 22 or interferometer 10 for each of the frequency components of input beam 24. The measurement or probe beam generated in either beam-conditioner 22 or interferometer 10 is one component of beam 30, i.e., beam 30A wherein the effects of off-axis and/or on-axis aberrations on beam 30A at substrate 60 may be reduced. Beam 30 further comprises a return reflected/scattered measurement beam 30B that is generated by the reflection/scattering of the measurement beam component 30A by substrate 60. The return measurement beam component 30B is combined with the reference beam in interferometer 10 to form a mixed beam wherein off-axis and/or on-axis aberrations may be reduced. In certain embodiments, the mixed beam with off-axis and/or on-axis aberrations reduced or not reduced is incident on a thin fluorescent layer or array of fluorescent spots and output beam 34 comprises an optical interference beam generated by fluorescence. In certain other embodiments, output beam 34 comprises the mixed optical beam.

Output beam 34 is detected by detector 70 to generate an electrical interference signal 72 from either the optical interference beam generated by fluorescence from the mixed output beam in the certain embodiments or from the mixed optical beam in the certain other embodiments. The composition of the thin fluorescent layer or array of fluorescent spots is selected such that the decay time of the fluorescence is much shorter than the read out time of detector 70.

Detector 70 may comprise in the certain other embodiments an analyzer to select common polarization states of the reference and return measurement beam components of beam 34 to form a mixed beam in lieu of beam 34 being formed as a mixed beam.

Substrate 60 is translated by stage 90 wherein substrate 60 is mounted on wafer chuck 84 with wafer chuck 84 mounted on stage 90. The position of stage 90 is controlled by transducer 82 according to servo control signal 78 from electronic processor and controller 80. The position of stage 90 is measured by metrology system 88 and position information acquired by metrology system 88 is transmitted as signal 76 to electronic processor and controller 80 to generate an error signal for use in the position control of stage 90. Metrology system 88 may comprise for example linear displacement and angular displacement interferometers and cap gauges. The elevation and angular orientation of substrate 60 is controlled by transducers 86A and 86B according to servo control signal 78.

In practice wherein bi- or quad-homodyne detection methods are used, known phase shifts are introduced by either of two techniques between the reference and measurement beam components of mixed beam 34 generated by interferometer system 10 wherein effects of off-axis and/or on-axis aberrations may be reduced. In one technique, phase shifts are introduced between the reference and measurement beam components for each of the frequency components by beam-conditioner 22 as controlled by signal 74 from electronic processor and controller 80. In the second technique, phase shifts are introduced between the reference and measurement beam components of mixed beam 34 for each of the frequency components as a consequence of frequency shifts introduced to the frequency components of input beam 24 by beam-conditioner 22 as controlled by signal 74 from electronic processor and controller 80.

In the practice wherein N-dimensional bi- and quad-homodyne detection methods are used, additional phase shifts are introduced between each corresponding reference and measurement beam portion of N portions of the mixed beam generated by interferometer 10. The additional phase shifts are in addition to those introduced in the implementation of bi- or quad-homodyne detection methods. The additional phase shifts are generated in interferometer 10 by causing changes in the locations of elements of the adaptive catoptric surfaces.

Figure 1B:
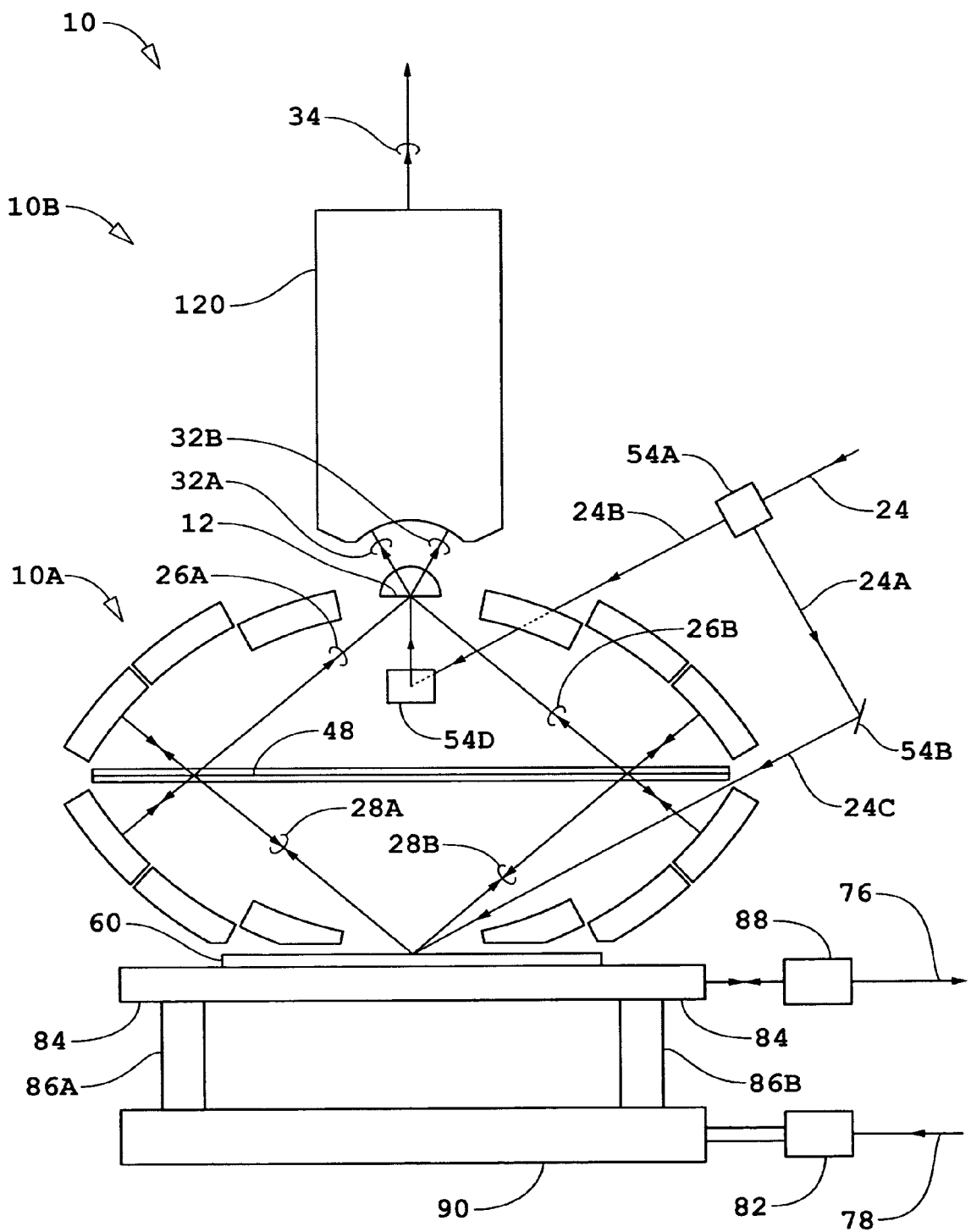
FIG. 1b is a schematic diagram of an interferometric non-confocal microscope system operating in a reflection mode that uses a catoptric imaging system.

Interferometer 10 of the first embodiment of the present invention is shown schematically in FIG. 1*b*. Interferometer 10 of the first embodiment comprises a first imaging system generally indicated as numeral 10A, interface 12 wherein effects of off-axis aberrations may be reduced, and a second imaging system generally indicated as numeral 10B. The second imaging system 10B may comprise a low power microscope having a large working distance, e.g. Nikon ELWD and SLWD and Olympus LWD, ULWD, and ELWD objectives or a high resolution catadioptric imaging system such as described in cited U.S. Pat. No. 6,552,852 (ZI-38) and U.S. Pat. No. 6,717,736 (ZI-43).

The first imaging system 10A is a catoptric imaging system that is a variant of catoptric and catadioptric imaging systems such as described in cited U.S. Pat. No. 6,552,852 (ZI-38) and U.S. Pat. No. 6,717,736 (ZI-43); U.S. Provisional Patent Applications No. 60/447,254 (ZI-40), No. 60/448,360 (ZI-41), No. 60/448,250 (ZI-42), No. 60/442,982 (ZI-45), No. 60/459,425, (ZI-50), No. 60/485,255 (ZI-53), No. 60/501,666 (ZI-54) and No. 60/506,715 (ZI-56); and U.S. patent application Ser. No. 10/778,371 (ZI-40), Ser. No. 10/782,057 (ZI-41), Ser. No. 10/782,058 (ZI-42), Ser. No. 10/765,229 (ZI-45), Ser. No. 10/816,180 (ZI-50), Ser. No. 10/886,157 (ZI-53), Ser. No. 10/938,408 (ZI-54), and Ser. No. 10/948,959 (ZI-56). Catoptric imaging system 10A is shown schematically in FIG. 1*c* with adaptive reflective surfaces 42A-1, 42A-2, 42A-3, 42C-1, 42C-2, 42C-3, 46A-1, 46A-2, 46A-3, 46C-1, 46C-2, and 46C-3. The adaptive reflective surfaces with transducers and servo control signals are shown schematically in FIG. 1*d*. Catoptric imaging system 10A further comprises beam-splitter 48 and interface 12 that may be configured to reduce the effects of off-axis aberrations.

Reflecting surfaces 42A-1, 42A-2, 42C-1, and 42C-2 comprise nominally a first single concave reflecting surface and reflecting surfaces 42A-3 and 42C-3 comprise nominally a second single concave reflecting surface. The first and second single concave reflecting surfaces have the same nominal centers of curvature. Reflecting surfaces 46A-1, 46A-2, 46C-1, and 46C-2 comprise nominally a third single concave reflecting surface and reflecting surfaces 46A-3 and 46C-3 comprise nominally a fourth single concave reflecting surface. The third and fourth concave reflecting surfaces have the same nominal centers of curvature. The centers of curvatures of the first and second concave reflective surfaces are the same as the conjugate of the centers of curvatures of the third and fourth concave reflective surfaces generated by beam-splitter 48. Accordingly, the centers of curvatures of the third and fourth concave reflective surfaces are the same as the conjugate of the centers of curvatures of the first and second concave reflective surfaces generated by beam-splitter 48.

The first and second concave reflective surfaces and the third and fourth concave reflective surfaces correspond to Fresnel mirrors of a catoptric imaging system such as described in cited U.S. Pat. No. 6,717,736 (ZI-43).

Figure 1C:
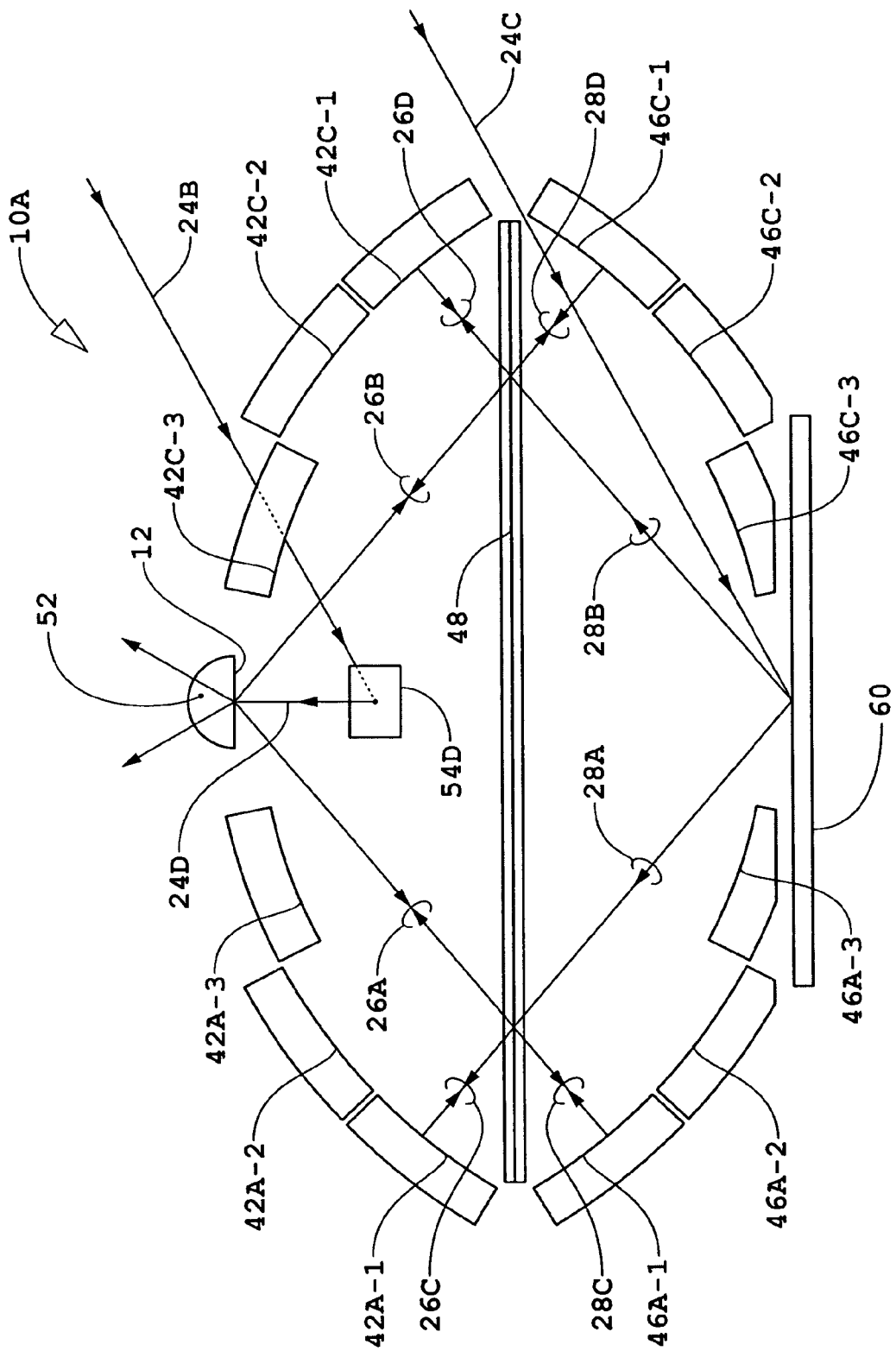
FIG. 1c is a diagram of a catoptric imaging system comprising a pellicle beam-splitter and adaptive catoptric reflecting surfaces.

Adaptive reflecting surfaces 42A-1, 42A-2, 42A-3, 42C-1, 42C-2, and 42C-3 and adaptive reflecting surfaces 46A-1, 46A-2, 46A-3, 46C-1, 46C-2 and 46C-3 shown in FIG. 1*c* may each be representative of annular rings or of sections of annular rings. The remaining description of the first embodiment will be based on a simple configuration wherein there are no additional reflecting surfaces beyond those described as a non-limiting example without departing from the scope and spirit of the present invention. The number of corresponding adaptive reflecting surfaces defines of the range of values of N that may be used in the N-dimensional bi- or quad-homodyne detection methods. In a non-limiting example of the simple configuration shown in FIG. 1*c*, the maximum value for N is 6.

Figure 1D:
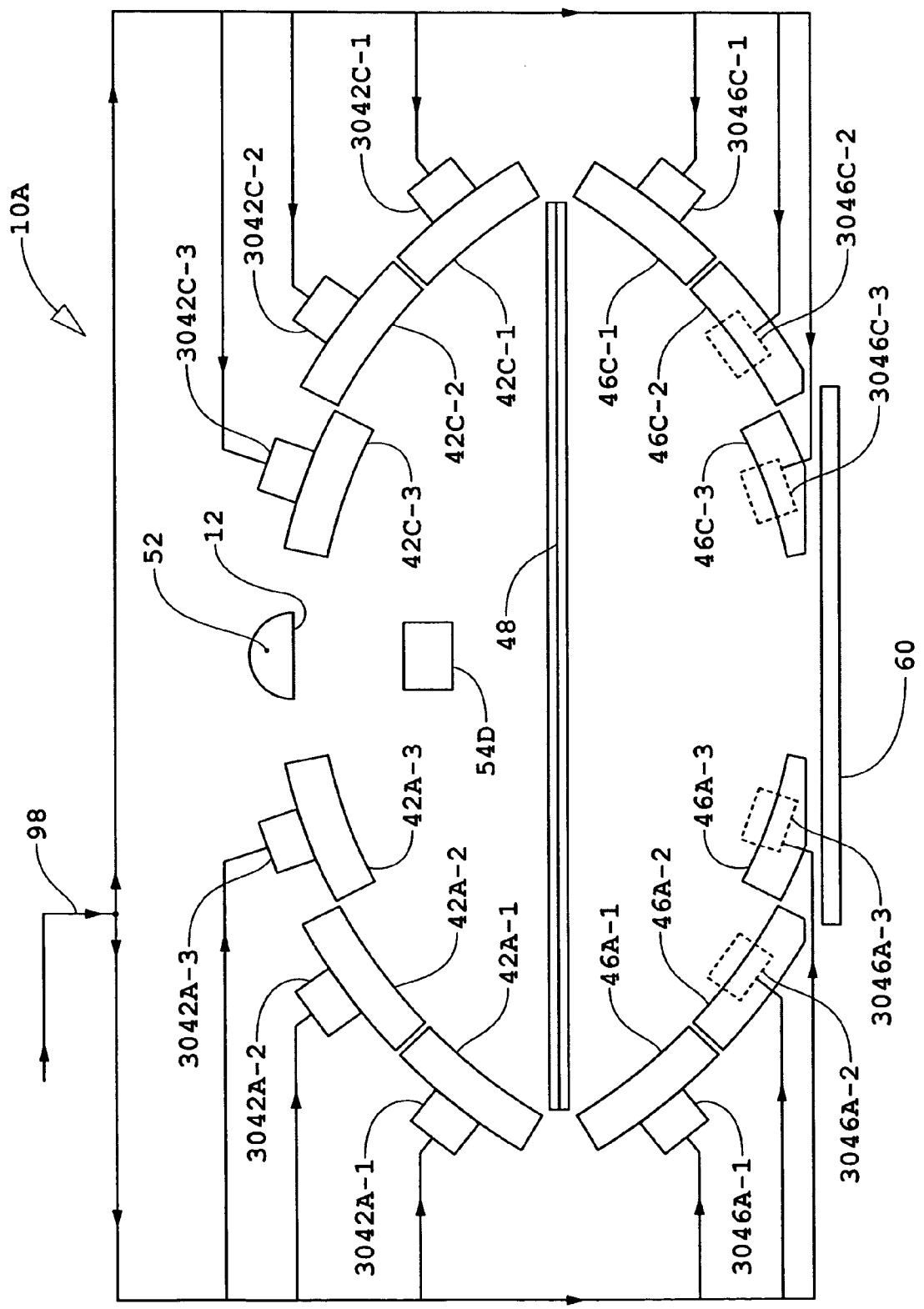
FIG. 1d is a diagram of a catoptric imaging system comprising a pellicle beam-splitter and adaptive catoptric surfaces attached to displacement transducers.

Referring to FIG. 1*d*, the locations and orientations of adaptive reflecting surfaces are controlled by transducers according to servo control signal 98. The description of servo control signal 98 is the same as the corresponding description of servo control signal 98 from servo controller 96 shown in FIG. 1*a*. For each of the adaptive reflective surfaces 42A-1, 42A-2, 42A-3, 42C-1, 42C-2, 42C-3, 46A-1, 46A-2, 46A-3, 46C-1, 46C-2, and 46C-3, there are corresponding transducers 3042A-1, 3042A-2, 3042A-3, 3042C-1, 3042C-2, 3042C-3, 3046A-1, 3046A-2, 3046A-3, 3046C-1, 3046C-2, and 3046C-3, respectively. Each of the transducers comprises three transducers that can either change the radial position of a corresponding adaptive reflective surface or effect changes in the orientation of the corresponding adaptive reflective surface in two orthogonal planes. The two orthogonal planes intersect in a line that is parallel to the optical axis of the corresponding adaptive reflective surface. Certain of the transducers are located so as to not interfere with substrate 60 and are indicate as dashed lines in FIG. 1*d*.

The working distance of interferometer 10 in FIG. 1*b* can be increased for example by removing the adaptive reflective surfaces 46A-3, 46C-3, 42A-3, and 42C-3 at the expense of increasing the size of the central obstruction presented to beams reflected/scattered or transmitted by the catoptric imaging system.

Convex lens 52 has a center of curvature the same as the common centers of curvature of the third and fourth single concave surfaces. Convex lens 52 is bonded together with interface 12. Interface 12 serves the function of the beam combining beam-splitter in interferometer 10 and may reduce the effects of off-axis aberrations. The second imaging system 10B is designed to image interface 12 onto the photosensitive surface of detector 70. The wavelength of beam 32 comprising beams 32A and 32B (see FIG. 1b) that is generated by interface 12 comprising a thin fluorescent layer or array of fluorescent spots will in general be in the visible that simplifies the design of the second imaging system 10B and detector 70. The composition of the thin fluorescent layer or array of fluorescent spots of interface 12 is selected such that the decay time of the fluorescence of the thin fluorescent layer or array of fluorescent spots is significantly less than the read out time of detector 70.

Referring to FIG. 1b, input beam 24 is incident on a non-polarizing beam-splitter 54A wherein a first portion thereof is reflected as a measurement beam 24A and a second portion of input beam 24 incident on non-polarizing beam-splitter 54A is transmitted as reference beam 24B. Measurement beam 24A is reflected by mirror 54B as measurement beam 24C. Reference beam 24B is incident on interface 12 after reflection by mirror 54D. When input beam 24 comprises non-coextensive reference and measurement beams, element 54A functions as mirror to reflect the measurement beam component of beam 24 as beam 24A and the reference beam component beam 24B of beam 24 is not incident on element 54A.

Measurement beam 24D or probe beam is incident on substrate 60 and portion thereof are reflected/scattered to form reflected/scattered measurement beams 28A and 28B (see FIG. 1c). Measurement beam 24D and reflected/scattered measurement beams 28A and 28B comprise measurement beam 30 shown in FIG. 1a. Measurement beam 28A is incident on beam-splitter 48 and first and second portions thereof are transmitted and reflected, respectively, as components of beams 26C and 28C, respectively. The description of the subsequent propagation of the components of beams 26C and 28C will be in terms of N portions wherein the description of each portion of the N portions is substantially the same. The portions of the components of beams 26C and 28C corresponding to one of the portions of the N portions that are subsequently reflected by reflective surfaces 42A-1 and 46A-1, respectively, are portions of components of beams 26C and 28C, respectively, directed toward beam-splitter 48. First and second portions of components of beam 26C directed toward beam-splitter 48 are reflected and transmitted, respectively, as components of beam 26A and 28A, respectively. First and second portions of components of beam 28C directed toward beam-splitter 48 are transmitted and reflected, respectively, as components of beam 26A and 28A, respectively.

The amplitude A of beam 26A comprising the first portions of beams 26E and 28E reflected and transmitted by beam-splitter 48, respectively, relative to the amplitude of the corresponding portion of beam 28A is given by the equation $$A = T(\nu)^{1/2} R(\nu)^{1/2} (1 + \cos \phi) \qquad (1)$$

where $\nu$ is an angle of incidence at beam-splitter 48 of the first portions of beams 26C and 28C reflected and transmitted by beam-splitter 48, respectively, and $T(\nu)^{1/2}$ and $R(\nu)^{1/2}$ are the complex transmission and reflection amplitude coefficients, respectively, and $\phi$ is the relative phase shift between the first portions of beams 26C and 28C reflected and transmitted, respectively, by beam-splitter 48. A maximum value for the amplitude A is obtained by the adjustment of the relative radial positions of reflective surfaces 42A-1 and 46A-1 to achieve the condition $$\phi = 0, 2\pi 4\pi, \ldots \qquad (2)$$

The condition is achieved by control of respective transducers with signal 98 from servo controller 96.

Catoptric imaging system 10A is functionally equivalent to the imaging properties of an interface wherein the index of refractions on the two sides of the interface are 1 and −1, respectively, when there is constructive interference between the measurement beam components of beam 26A and between the measurement beam components of beam 26B. When there is constructive interference between the measurement beam components, the complex amplitude of the interferometric conjugate image relative to the amplitude that would be achieved by a lossless otherwise equivalent imaging system with respect to pupil function is equal to $$2T(\nu)^{1/2} R(\nu)^{1/2}. \qquad (3)$$

The combination of a reflection and a transmission for each ray of the converging beams forming the interferometric conjugate image of substrate 60 substantially compensates for departure of properties of beam-splitter 48 from properties of an ideal beam-splitter. The compensation is demonstrated by Eq. (3). Function $T(\nu)^{1/2} R(\nu)^{1/2}$ has a maximum at $T(\nu) = R(\nu) = 1/2$ and has only a second order dependence on changes of the transmission/reflection properties, i.e.

$$[T(\nu)^{1/2} - 1/\sqrt{2}][R(\nu)^{1/2} - 1/\sqrt{2}].$$

The average intensity transmission of the first embodiment is increased by a factor of 2 as demonstrated by Eq. (3) than would otherwise be obtained as a result of the constructive interference of beams formed by the two different paths through the imaging system of the first embodiment. The constructive interference is achieved in the first embodiment by the adjustment of the relative radial positions of conjugate adaptive reflective surfaces by servo control signal 98. The determination of the correct values for the servo control signal 98 is made during an initialization period of the first embodiment by adjusting for example the relative servo control signal components for corresponding conjugate adaptive reflective surfaces to yield a maximum value in the amplitude of the conjugate image. Other techniques can be used for the determination of the correct values for the components of servo control signal 98 such as introducing phase modulations at a set of non-redundant frequencies and measuring the amplitudes of components of transmitted beams at the non-redundant frequencies.

Manufacture of High Precision Adaptive Reflective Surfaces: Replication

Adaptive reflective surfaces 42A-1, 42A-2, 42A-3, 42C-1, 42C-2, 42C-3, 46A-1, 46A-2, 46A-3, 46C-1, 46C-2, and 46C-3 can be generated by standard optical grinding and polishing techniques. However, improved performance for the catoptric imaging system 10A is achieved at a lower cost by generating the adaptive reflective surfaces by the process of replication. Masters used in the replication process are selected as the best portion of surfaces such as the first or third single concave surfaces and such as the second or fourth single concave surfaces. The masters or secondary masters generated from the masters by replication of first negative replications and then positive replications are first coated with a release agent, reflective layers comprising a single or multiple layers are deposited on the release agent coated surfaces, and than backing elements are applied to the reflecting layers by a bonding agent. After the bonding agent is cured, the backing elements, the cured bonding agent, and the reflective layer are separated from the masters or secondary masters at the release agent interface. Thus, adaptive reflective surfaces 42A-1, 42A-2, 42A-3, 42C-1, 42C-2, 42C-3, 46A-1, 46A-2, 46A-3, 46C-1, 46C-2, and 46C-3 are manufactured with surface figures that have a significantly higher precision than the precision of single surfaces corresponding to the first, second, third, and fourth single concave surfaces.

Use of Conjugate Adaptive Reflective Surfaces as Optical Switches

Each conjugate pair of adaptive reflective surfaces 42A-1, 42A-2, 42A-3, 42C-1, 42C-2, 42C-3, 46A-1, 46A-2, 46A-3, 46C-1, 46C-2, and 46C-3 have been described in terms of maximizing the corresponding portions of amplitudes of beams 26A and 26B [see discussion associated with respect to Eq. (1)]. It is apparent on examination of Eq. (1) that each of the conjugate pairs of adaptive reflective surfaces may also be used as an optical switch by adjusting the corresponding $\phi$ such that $$\phi = \pi, 3\pi, \ldots \quad (4)$$

The condition expressed by Eq. (4) is achieved by control of respective transducers with signal 98 from servo controller 96.

The optical switch mode of operation of the conjugate pairs of adaptive reflective surfaces can be beneficially used in initialization phases of the first embodiment of the present invention. For example, in the initialization phase for the determination of the correct relative phases of conjugate pairs of adaptive reflective surfaces, properties of a pair of conjugate surfaces of the array of conjugate pairs can be individually measured by switching off the complimentary set of array of conjugate pairs.

The optical switch mode of operation of the conjugate pairs of adaptive reflective surfaces can also beneficially be use to switch from different modes of operation of the first embodiment of the present invention. The different modes of operation may comprise different values for N.

Use of Conjugate Adaptive Reflective Surfaces as Phase Shifters

Phases of portions of beam 26A and 26B associated with adaptive reflective surfaces 42A-1, 42A-2, 42A-3, 42C-1, 42C-2, 42C-3, 46A-1, 46A-2, 46A-3, 46C-1, 46C-2, and 46C-3 may be shifted in the first embodiment of the present invention by adjusting the radial positions of the adaptive reflective surfaces 42A-1, 42A-2, 42A-3, 42C-1, 42C-2, 42C-3, 46A-1, 46A-2, 46A-3, 46C-1, 46C-2, and 46C-3 while maintaining the condition given by Eq. (2). In particular, the phases of portions of 26A and 26B associated with adaptive reflective surfaces 42A-1, 42A-2, 42A-3, 42C-1, 42C-2, 42C-3, 46A-1, 46A-2, 46A-3, 46C-1, 46C-2, and 46C-3 may be shifted between the values of $$0 \text{ and } \pi. \quad (5)$$

This phase shifting feature is used in the implementation of the subsequently described N-dimensional bi- and quad-homodyne detection methods.

Differential Measurements

The phase shift feature of the first embodiment of the present invention described with respect to Eq. (5) can be used to obtain differential measurements of properties of the measurement beams reflected/scattered by substrate 60. The differential measurements are with respect to changes of the amplitudes of the measurement beams reflected/scattered by substrate 60 as a function of reflection/scattering angle.

The Use of Conjugate Adaptive Reflective Surfaces To Compensate For On-Axis Aberrations When a plane section of substrate 60 that is being imaged by interferometer 10 of the first embodiment of the present invention is embedded below the surface of substrate 60, on-axis aberrations will be introduced such as described in commonly owned U.S. Provisional Patent Application No. 60/444,707 (ZI-44) entitled "Compensation for Effects of Mismatch in Indices of Refraction at a Substrate-Medium Interface in Confocal and Interferometric Confocal Microscopy" and U.S. patent application Ser. No. 10/771,785 (ZI-44) entitled "Compensation for Effects of Mismatch in Indices of Refraction at a Substrate-Medium Interface in Confocal and Interferometric Confocal Microscopy" wherein both the provisional and non-provisional patent applications are by Henry A. Hill and the contents of which are herein incorporated in their entirety by reference. On-axis aberrations may also be introduced by a pellicle beam-splitter or aperture-array beam-splitter. Certain of the on-axis aberrations are compensated in catoptric imaging system 10A by changing the focal lengths of conjugate pairs of adaptive reflective surfaces 42A-1, 42A-2, 42A-3, 42C-1, 42C-2, 42C-3, 46A-1, 46A-2, 46A-3, 46C-1, 46C-2, and 46C-3. The certain of the on-axis aberrations may be reduced to generate a diffraction limited spot on substrate 60 and/or in the image space of a catoptric imaging system to obtain diffraction limited information about a spot on substrate 60. The focal lengths of the conjugate pairs of adaptive reflective surfaces are adjusted by changing the radial locations of the conjugate pairs of adaptive reflective surfaces 42A-1, 42A-2, 42A-3, 42C-1, 42C-2, 42C-3, 46A-1, 46A-2, 46A-3, 46C-1, 46C-2, and 46C-3.

The surfaces represented by adaptive reflective surfaces 42A-1, 42A-2, 42A-3, 42C-1, 42C-2, and 42C-3 are changed in compensating for the effects of the spherical aberrations from a nominally spherical surface to a nominal aspherical surface. Also the surfaces represented by adaptive reflective surfaces 46A-1, 46A-2, 46A-3, 46C-1, 46C-2, and 46C-3 are changed in compensating for the effects of the spherical aberrations from a nominally spherical surface to a nominal aspherical surface.

Use of Conjugate Adaptive Reflective Surfaces to Generate Vertical and Lateral Scans A vertical scan of plane sections of substrate 60 is implemented in the first embodiment of the present invention by scanning the focal lengths of conjugate pairs of adaptive reflective surfaces 42A-1, 42A-2, 42A-3, 42C-1, 42C-2, 42C-3, 46A-1, 46A-2, 46A-3, 46C-1, 46C-2, and 46C-3. The focal lengths of the conjugate pairs of adaptive surfaces are adjusted by scanning the radial locations of the conjugate pairs of adaptive surfaces 42A-1, 42A-2, 42A-3, 42C-1, 42C-2, 42C-3, 46A-1, 46A-2, 46A-3, 46C-1, 46C-2, and 46C-3.

A lateral scan of a plane section of substrate 60 is implemented in the first embodiment of the present invention by scanning the centers of curvature of adaptive reflective surfaces 42A-1, 42A-2, 42A-3, 42C-1, 42C-2, 42C-3, 46A-1, 46A-2, 46A-3, 46C-1, 46C-2, and 46C-3. The centers of curvatures of the adaptive surfaces are adjusted by scanning the angular orientations of the adaptive reflective surfaces 42A-1, 42A-2, 42A-3, 42C-1, 42C-2, 42C-3, 46A-1, 46A-2, 46A-3, 46C-1, 46C-2, and 46C-3.

The bandwidth of the speeds of the vertical and lateral scans of substrate 60 are determined in the first embodiment by the bandwidth of the scanning speeds in radial positions and angular orientations, respectively, of the adaptive reflective surfaces 42A-1, 42A-2, 42A-3, 42C-1, 42C-2, 42C-3, 46A-1, 46A-2, 46A-3, 46C-1, 46C-2, and 46C-3. The bandwidths of the scanning speeds of the adaptive reflective surfaces will generally be orders of magnitude larger than either the bandwidth of vertical and lateral scans that can be generated by translating the interferometer system 10 and detector system 70 or the bandwidth of vertical and lateral scans that can be generated by physically translating the vertical and lateral position of substrate 60 and wafer chuck 84.

Periodically Stationary Images Of A Scanning Object Or Substrate

The use of multi-element adaptive catoptric imaging systems makes it possible to introduce a mode of operation such that the image of a plane section of an object or substrate 60 is fixed in an image plane for a short period of time, i.e., instantaneously stationary, that covers the time span of a beam pulse generating the image although the plane section of the object is moving in the object space at either a low or high slew rate. The instantaneously stationary image of a scanning object is obtained by using the property described in the earlier section entitled "Use of Conjugate Adaptive Reflective Surfaces to Generate Vertical and Lateral Scans." The conjugate adaptive reflective surfaces are driven to introduce a lateral scan of the image of interface 12 in the plane section of the object with a scan speed equal to the scan speed of substrate 60 during the period of a pulse of source 18.

The sequence of periods when the image of interface 12 in the plane section of the object or substrate 60 are moving collinearly will correspond to the sequence of periods of the pulses of source 18. For a pulse train that is uniform in time, the periods of stationary images of a scanning substrate 60 will be periodic in time.

Alternatively, interface 12 may be scanned such the image of interface 12 in the plane section of substrate 60 is stationary during a sequence of pulses of source 18.

N-Dimensional Bi- and Quad-Homodyne Detection Methods

The description of source 18 including a pulse mode of operation and beam-conditioner 22 is the same as the corresponding portions of the description given to the source and beam-conditioner in embodiments described in commonly owned U.S. Provisional Patent Application No. 60/442,858 (ZI-47) entitled "Apparatus and Method for Joint Measurements of Conjugated Quadratures of Fields of Reflected/Scattered Beams by an Object in Interferometry" and U.S. patent application Ser. No. 10/765,368 (ZI-47) entitled "Apparatus and Method for Joint Measurements of Conjugated Quadratures of Fields of Reflected/Scattered or Transmitted Beams by an Object in Interferometry" wherein the provisional and the non-provisional patent applications are by Henry A. Hill and the contents of which are herein incorporated in their entirety by reference and in cited U.S. Provisional Patent Applications No. 60/485,255 (ZI-53) and No. 60/602,046 (ZI-57) and in cited U.S. patent application Ser. No. 10/886,157 (ZI-53) and U.S. Patent Application filed Aug. 16, 2005 (ZI-57) entitled "Apparatus and Method for Joint And Time Delayed Measurements of Components of Conjugated Quadratures of Fields of Reflected/Scattered and Transmitted/Scattered Beams by an Object in Interferometry."

The descriptions the of bi-homodyne and quad-homodyne detection methods of the first embodiment of the present invention are the same as corresponding portions of the descriptions given for the descriptions of bi-homodyne and quad-homodyne detection methods in the cited U.S. Provisional Patent Application Nos. 60/442,858 (ZI-47) and 60/485,255 (ZI-53) and in cited U.S. patent application Ser. Nos. 10/765,368 (ZI-47) and 10/886,157 (ZI-53) wherein the homodyne detection methods are based on frequency encoding. The extension of the bi- and quad-homodyne detection methods to N-dimensional bi- and quad-homodyne detection methods based on a combination of frequency encoding and either amplitude or phase modulations or permutations is implemented in the first embodiment by the use of the conjugate pairs of adaptive reflective surfaces of catoptric imaging system 10A as optical switches or as $\pi$ phase shifters, respectively. The extension of the bi- and quad-homodyne detection methods to N-dimensional bi- and quad-homodyne detection methods may also be based on a combination of frequency encoding, polarization encoding, and either amplitude or phase modulations or permutations. The description of bi- and quad-homodyne detection methods based on a combination of frequency and polarization encoding is the same as the corresponding description given in cited U.S. Provisional Patent Application No. 60/459,425 (ZI-50) and in cited U.S. patent application Ser. No. 10/816,180 (ZI-50).

The N-dimensional bi- and quad-homodyne detection methods are homodyne detection methods that exhibit the same properties as the cited bi- and quad-homodyne detection methods with respect to making joint measurements of conjugated quadratures of fields: a joint measurement of a conjugated quadratures of fields is made in the bi- and quad-homodyne detection methods and joint measurements are made of N independent conjugated quadratures of fields in the N-dimensional bi- and quad-homodyne detection methods where N is an integer. The (i,k) electrical interference signal $\Sigma_{i,k}$, $1 \le i \le N$ and $1 \le k \le 4$, is written in terms of the contribution $S_{i,j,k}$ that corresponds to portion j of the N portions of electrical interference signal $\Sigma_{i,k}$ associated with the conjugate pairs of adaptive reflective surfaces 42A-1, 42A-2, 42A-3, 42C-1, 42C-2, 42C-3, 46A-1, 46A-2, 46A-3, 46C-1, 46C-2, and 46C-3. The representation of $\Sigma_{i,k}$ in terms of $S_{i,j,k}$ is expressed as $$\Sigma_{i,k} = \sum_{j=1}^{N} h_{ij} S_{i,j,k}, \ 1 \le i \le N, \ 1 \le k \le 4 \qquad (6)$$

where $h_{ij}$ are matrix elements $H=(h_{ij})$ are constants.

The values of matrix elements $h_{ij}$ are selected and controlled by conjugate adaptive reflective surfaces operating in either the phase shifting mode or the optical switching mode. In the phase shifting mode, the values of $h_{ij}$ are selected to be $\pm 1$ which corresponds to use of phase modulations or permutations. In the optical switching mode, the matrix elements $h_{ij}$ are selected to be either 0 or 1 which corresponds to amplitude modulations or permutations. In the case of phase modulations, the measurement of each of the N independent conjugated quadratures is made as a joint measurement and the N independent conjugated quadratures may be jointly measured with respect to each other. In the case of amplitude modulations, the measurement of each of the N independent conjugated quadratures is made as a joint measurement although the N independent conjugated quadratures are not jointly measured with respect to each other.

There are 4N values of electrical interference signal $\Sigma_{i,k}$ measured for each spot in or on substrate 60 that is being imaged. The number of different values of the electrical interference signal $\Sigma_{i,k}$ that is measured is 4 times the number of independent conjugated quadratures that are being measured because there are 2N independent components of conjugated quadratures measured and two measurements of electrical interference signal values are required for each independent component of conjugated quadratures. For further discussion, reference is made to the bi-homodyne detection method such as described in cited U.S Provisional Patent Application No. 60/442,858 (ZI-47) and U.S. patent application Ser. No. 10/765,368 (ZI-47) and in commonly owned U.S. Provisional Patent Application No. 60/485,507 (ZI-52) and U.S. patent application Ser. No. 10/886,010 (ZI-52) wherein conjugated quadratures of scattered/reflected or scattered/transmitted fields are obtained jointly with a set of four electrical interference signal values obtained for each spot on and/or in a substrate being imaged. The latter cited provisional and non-provisional application are both entitled "Apparatus And Method For High Speed Scan For Detection And Measurement of Properties of Sub-Wavelength Defects And Artifacts In Semiconductor And Mask Metrology" and both are by Henry A. Hill, the contents of each are incorporated herein in their entirety by reference.

The contribution $S_{i,j,k}$ is represented for the bi-homodyne detection method within a scale factor by the formula $$S_{i,j,k} = P_{i,k} \sum_{m=1}^{2} \begin{Bmatrix} \xi_{i,k}^2 |A_{j,m}|^2 + \zeta_{i,k}^2 |B_{j,m}|^2 + \eta_{i,k}^2 |C_{j,m}|^2 + \\ \zeta_{i,k}\eta_{i,k} 2|B_{j,m}||C_{j,m}|\cos\varphi_{B_{j,m}C_{j,m}}\varepsilon_{m,k} + \\ \xi_{i,k}\zeta_{i,k} 2|A_{j,m}||B_{j,m}|\cos\varphi_{A_{j,m}B_{j,m}}\varepsilon_{m,k} + \\ \varepsilon_{m,k}\xi_{i,k}\eta_{i,k}[1-(-1)^m]|A_{j,m}||C_{j,m}|\cos\varphi_{A_{j,m}C_{j,m}} + \\ \varepsilon_{m,k}\xi_{i,k}\eta_{i,k}[1+(-1)^m]|A_{j,m}||C_{j,m}|\sin\varphi_{A_{j,m}C_{j,m}} \end{Bmatrix} \quad (7)$$

where coefficient $A_{j,m}$ represents the amplitude of the reference beam corresponding to pulse (i,k) of input beam 24 and to the frequency component of the input beam 24 that has index m; coefficient $B_{j,m}$ represents the amplitude of the background beam corresponding to reference beam $A_{j,m}$; coefficient $C_{j,m}$ represents the amplitude of the return measurement beam corresponding to reference beam $A_{j,m}$; $P_{i,k}$ represents the integrated intensity of the first frequency component of the input beam 24 pulse (i,k) of a sequence of 4N pulses; and an example set of values for $\varepsilon_{m,k}$ are listed in Table 1. There are other sets of values for $\varepsilon_{m,k}$ that may be used in certain embodiments of the present invention wherein the other set of values for $\varepsilon_{m,k}$ satisfy the conditions set out in subsequent Eqs. (8) and (9) herein.

The change in the values of $\varepsilon_{m,k}$ from 1 to $-1$ or from $-1$ to 1 corresponds to changes in relative phases of respective reference and measurement beams. The coefficients $\xi_{i,k}$, $\zeta_{i,k}$, and $\eta_{i,k}$ represent effects of variations in properties of a conjugate set of 4N pinholes such as size and shape if used in the generation of the spot on and/or in substrate 60, properties of a conjugate set of 4N pinholes such as size and shape if used at a conjugate set of 4N detector pixels corresponding to the spot on and/or in substrate 60, and the sensitivities of the conjugate set of 4N detector pixels for the reference, background, and the return measurement beam, respectively. In a

TABLE 1

| | $\varepsilon_{m,k}$ | |
|---|---|---|
| | m | |
| k | 1 | 2 |
| 1 | 1 | 1 |
| 2 | 1 | −1 |
| 3 | −1 | −1 |
| 4 | −1 | 1 | bi-homodyne detection method operating in a non-scanning mode, the conjugate set of pinholes corresponds to a single pinhole or fluorescent spot of interface 12 and the conjugate set of four pixels corresponds to a single pixel. In a bi-homodyne detection method operating in a non-scanning mode, the conjugate set of four pinholes comprise pinholes or fluorescent spots of interface 12 that are conjugate to a spot in or on the substrate being imaged at different times during the scan.

An important requirement of $\varepsilon_{m,k}$ is that $$\sum_{k=1}^{4} \varepsilon_{m,k} = 0, \, m=1, 2. \quad (8)$$

Another important requirement is that the $\varepsilon_{m,k}$ are orthogonal over the range of m=1,2 for m≠m' since $\varepsilon_{m,k}$ and $\varepsilon_{m',k}$ are orthogonal over the range of k=1,2,3,4, i.e., $$\sum_{j=1}^{4} \varepsilon_{m,j}\varepsilon_{m',j} = 4\delta_{m,m'} \quad (9)$$

where $\delta_{m,m'}$ is the Kronecker delta defined by $$\delta_{m,m'} = 1 \text{ for } m = m', \quad (10)$$
$$\delta_{m,m'} = 0 \text{ for } m \neq m'.$$

A set of conditions that are used to derive the matrix elements $h_{i,j}$ for the phase modulation or permutation embodiment are that the values of $h_{i,j}$ are either ±1 and that $$\sum_{j=1}^{N} h_{i,j}h_{i',j} = N\delta_{i,i'}. \quad (11)$$

Three examples of matrices $H=(h_{i,j})$ which meet the requirements of the N-dimensional bi- and quad-homodyne detection methods when using phase modulations or permutations are as follows:

$$(h_{ij}) = \begin{pmatrix} 1 & 1 \\ 1 & -1 \end{pmatrix}, N = 2; \quad (12)$$

$$(h_{ij}) = \begin{pmatrix} 1 & 1 & 1 & 1 \\ 1 & -1 & 1 & -1 \\ 1 & 1 & -1 & -1 \\ 1 & -1 & -1 & 1 \end{pmatrix}, N = 4; \quad (13)$$

$$(h_{ij}) = \begin{pmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{pmatrix}, N = 8. \quad (14)$$

Note that the matrix $(h_{ij})$ for $N=2^p$ where p is an integer is generated from the matrix $(h_{ij})$ for $N=2^{p-1}$ and the matrix $(h_{ij})$ for $N=2$, i.e., for each matrix element of $(h_{ij})$ for $N=2$, substitute the matrix $(h_{ij})$ for $N=2^{p-1}$ multiplied by the respective matrix element of $(h_{ij})$ for $N=2$. This construction technique corresponds to the Sylvester construction [see Sylvester (1867)].

The matrix $H=(h_{ij})$ defined in the preceding discussions are Hadamard matrices of order N. Hadamard matrices are a class of square matrix invented by Silvester [J. J. Sylvester, London Edinburgh and Dublin *Philos. Mag. And J. Sci.*, 34, p 461 (1867)] under the name of anallagmatic pavement, 26 years before Hadamard [J. Hadamard, *Math Phys.* 12, p 311 (1893)] considered them. Hadamard matrices are common in signal processing and coding applications.

An N×N matrix $H=(h_{ij})$ is an Hadamard matrix of order N if the entries of are either ±1 and such that $HH^T=NI$ where $H^T$ is the transpose of H and I is the order N identity matrix. In other words, an N×N matrix with only +1 and -1 as its elements is Hadamard if the inner product of two distinct rows is 0 and the inner product of a row with itself is N, which is equivalent to the condition given by Eq. (11).

A Hadamard matrix of order N is a solution to Hadamar's maximum determinant problem, i.e., it has the maximum possible determinant (in absolute value) of any complex matrix with elements $|a_{ij}| \leq 1$ [J. Brenner and L. Cummings, *Amer. Math. Monthly* 79 p. 626 (1972)], namely $N^{N/2}$.

To obtain a matrix $(h_{ij})$ for N different from a value of $2^p$ by integer q, remove any q columns from the Hadamard matrix $H=(h_{ij})$ specified herein for $N=2^p$. For this case, matrix $(h_{ij})$ is a (N-q)×N rectangular matrix and N-q independent conjugated quadratures are measured jointly from 4N measured values of electrical interference signal $\Sigma_{i,k}$ for each spot in or on substrate 60 being imaged. In certain embodiments of the present invention, arrays of values of electrical interference signal $\Sigma_{i,k}$ are obtained simultaneously with an array of detector pixels to yield an array of N-q independent conjugated quadratures jointly measured for an array of spots in or on a section of substrate 60 being imaged.

The first step in the processing the measured values of $\Sigma_{i,k}$ for the conjugated quadratures specified by j=p, the corresponding $S_{i,p,k}$ term in $\Sigma_{i,k}$ are projected out or extracted from the measured $\Sigma_{i,k}$ to obtain four quantities by using the orthogonal properties of $h_{i,j}$ as expressed by Eq. (11). The four quantities are subsequently processed for the conjugated quadratures specified by j=p using the orthogonal properties of $\epsilon_{m,k}$ expressed by Eq. (9) such as described in cited U.S Provisional Patent Applications No. 60/442,858 (ZI-47) and No. 60/485,507 (ZI-52) and in cited U.S. patent applications Ser. No. 10/765,368 (ZI-47) and Ser. No. 10/886,010 (ZI-52). The procedure is repeated to obtain the other conjugated quadratures.

The advantages of the N-dimensional bi-homodyne and quad-homodyne detection methods are the same as the advantages of the bi-homodyne and quad-homodyne detection methods described in cited U.S. Provisional Patent Application Nos, 60/442,858 (ZI-47) and 60/485,507 (ZI-52) and in cited U.S. patent application Ser. No. 10/765,368 (ZI-47) and Ser. No. 10/886,010 (ZI-52).

The option of using the conjugate adaptive reflective surfaces as optical switches makes it possible to rapidly change the effective value of N from a maximum value to values less than the maximum value for either of the amplitude or phase modulation or permutation modes. For example, if the maximum value of N is 8, one can rapidly change from operating with a value of N=8 to a value of N=2.

The conditions that are used to derive the matrix elements $h_{i,j}$ for the amplitude modulation or permutation embodiment are that the values of $h_{i,j}$ be equal to either 0 or 1 and that the selection of the designs yield the best signal-to-noise ratios. In this case, the values of the matrix elements $h_{i,j}$ are derived for example from a binary simplex code [see M. Harwit and N. J. A. Sloane, *Hadamard Transform Optics* (Academic, New York, 1979)]. Using $s_{ij}$ to denote the matrix elements $h_{i,j}$ for the amplitude modulation or permutation, an example of a set of matrix elements $s_{ij}$ of order 7 is $$(s_{ij}) = \begin{pmatrix} 0 & 0 & 1 & 0 & 1 & 1 & 1 \\ 0 & 1 & 0 & 1 & 1 & 1 & 0 \\ 1 & 0 & 1 & 1 & 1 & 0 & 0 \\ 0 & 1 & 1 & 1 & 0 & 0 & 1 \\ 1 & 1 & 1 & 0 & 0 & 1 & 0 \\ 1 & 1 & 0 & 0 & 1 & 0 & 1 \\ 1 & 0 & 0 & 1 & 0 & 1 & 1 \end{pmatrix}. \quad (15)$$

The phase shift feature can be used to obtain differential measurements of properties of the measurement beams reflected/scattered by substrate 60. For an example of N=2 and the introduction of a relative phase shift π between the beams corresponding to the pair of conjugate adaptive reflective surfaces, the measured quantities correspond to a differential measurement, i.e., operation in a dark field mode.

In the first embodiment, interface 12 is formed of an array of thin fluorescent spots wherein there is no reduction of effects of off-axis aberrations. An example of a pattern of an array of thin fluorescent spots is the pattern of apertures shown in FIG. 1f with apertures 62 filed with a fluorescent medium, e.g., lumogen, to form thin fluorescent spots. The size and spacing of the apertures are a and b, respectively. The size of the apertures a may be less than or approximately equal to the resolution of imaging system 10A in certain end use applications or larger than the resolution in one or two dimensions in certain other end use applications such as described in cited U.S. Provisional Patent Application No. 60/485,507 (ZI-52) and U.S. patent application Ser. No. 10/886,010 (ZI-52). The shape of the apertures may be circular or some other shape such as slits.

Interface 12 comprising the array of sub-wavelength thin fluorescent spots also serves the function of a pinhole array beam-splitter in an interferometer wherein the description is the same as the corresponding description given in cited U.S. Provisional Patent Application No. 60/442,982 (ZI-45) and U.S. patent application Ser. No. 10/765,229 (ZI-45).

Interface 12 of the first embodiment which is not configured to reduce effects of off-axis aberrations is the simplest interface with respect to fabrication compared to the corresponding interface 12 of other embodiments and other variants of the present invention. However, the gain with respect to reduced complexity of fabrication is at the cost of having a reduced field of view for which diffraction limited information is obtained.

Figure 1E:
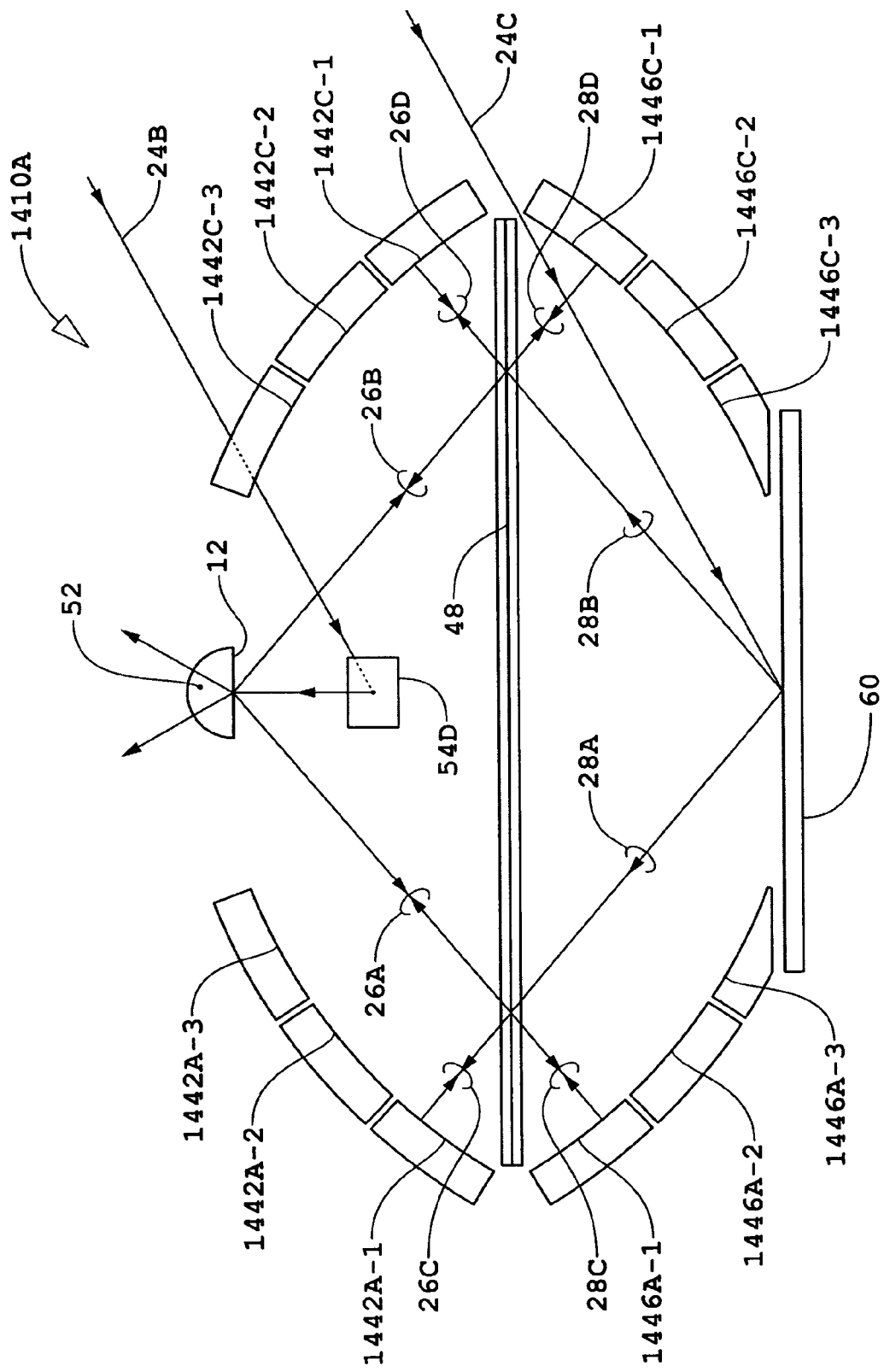
FIG. 1e is a schematic diagram of a catoptric imaging system of an interferometric non-confocal microscope system that uses a catoptric imaging system comprising a pellicle beam-splitter.
Figure 1F:
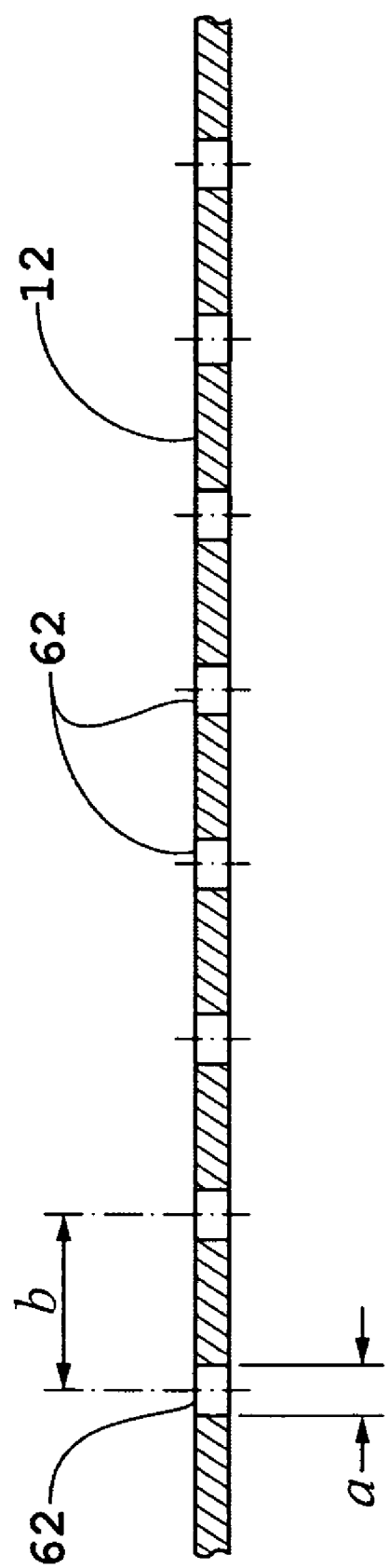
FIG. 1f is a schematic diagram of an array of thin fluorescent spots.
Figure 1G:
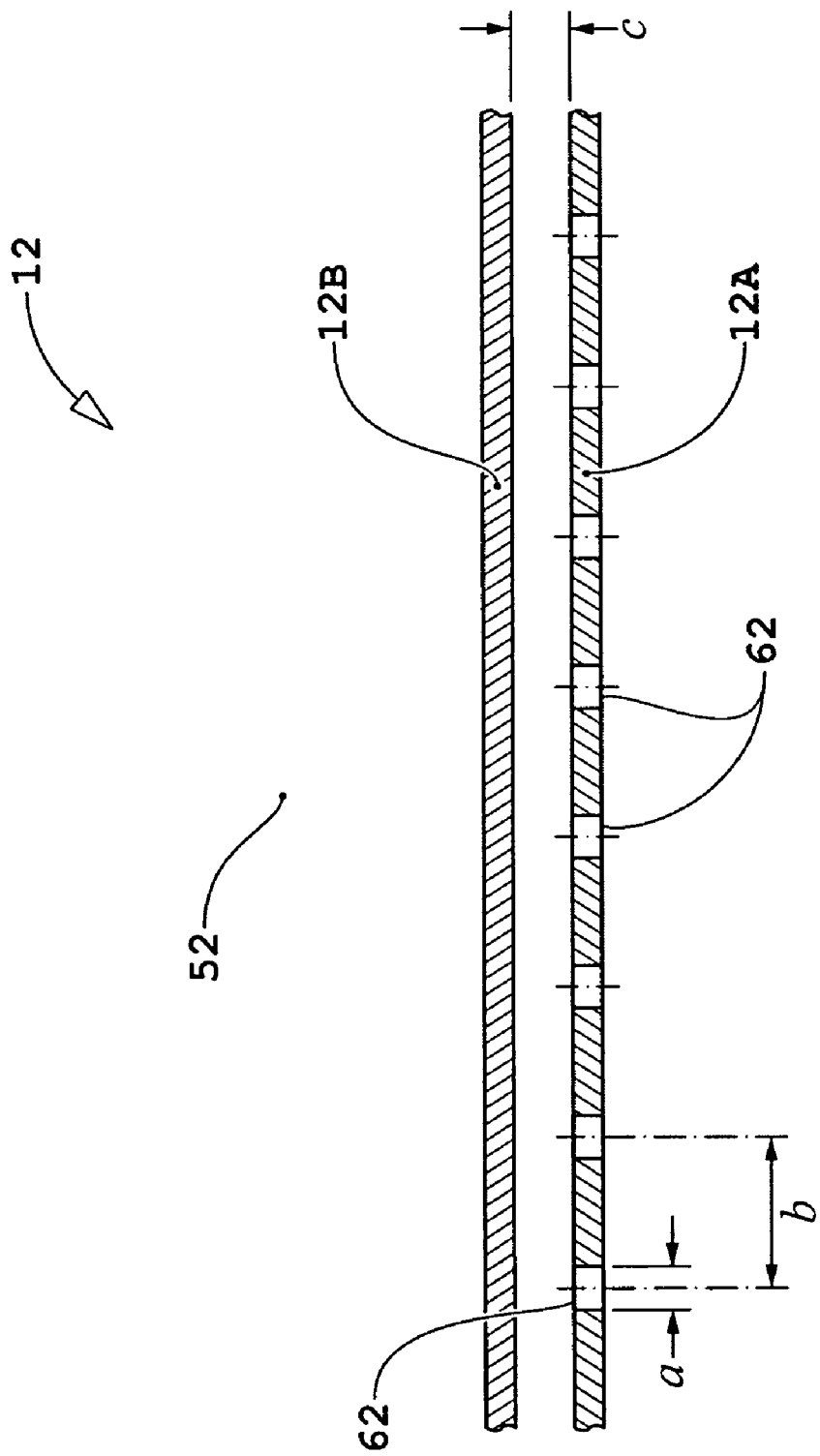
FIG. 1g is a schematic diagram of a thin fluorescent layer placed behind an array of pinholes.

A first variant of interface 12 is shown schematically in FIG. 1g in which no reduction of effects of off-axis aberrations is made. Interface 12 is formed with thin fluorescent layer 12B placed behind an array of pinholes 12A. The efficiency for detecting beams transmitted by pinhole array 12A can be increased by manufacturing pinhole array 12A with a reflective backside. The size of the spacing c between pinhole array 12A and thin fluorescent layer 12B is selected to optimize the efficiency for detection of beams transmitted by pinhole array 12A without significantly degrading the resolution beyond that required in an end use application. The description of the shape, size a, and spacing b of the pinholes in pinhole array 12A is the same as the corresponding portion of the description of the shape, size a, and spacing b of the apertures in interface 12 of the first embodiment of the present invention.

Figure 1H:
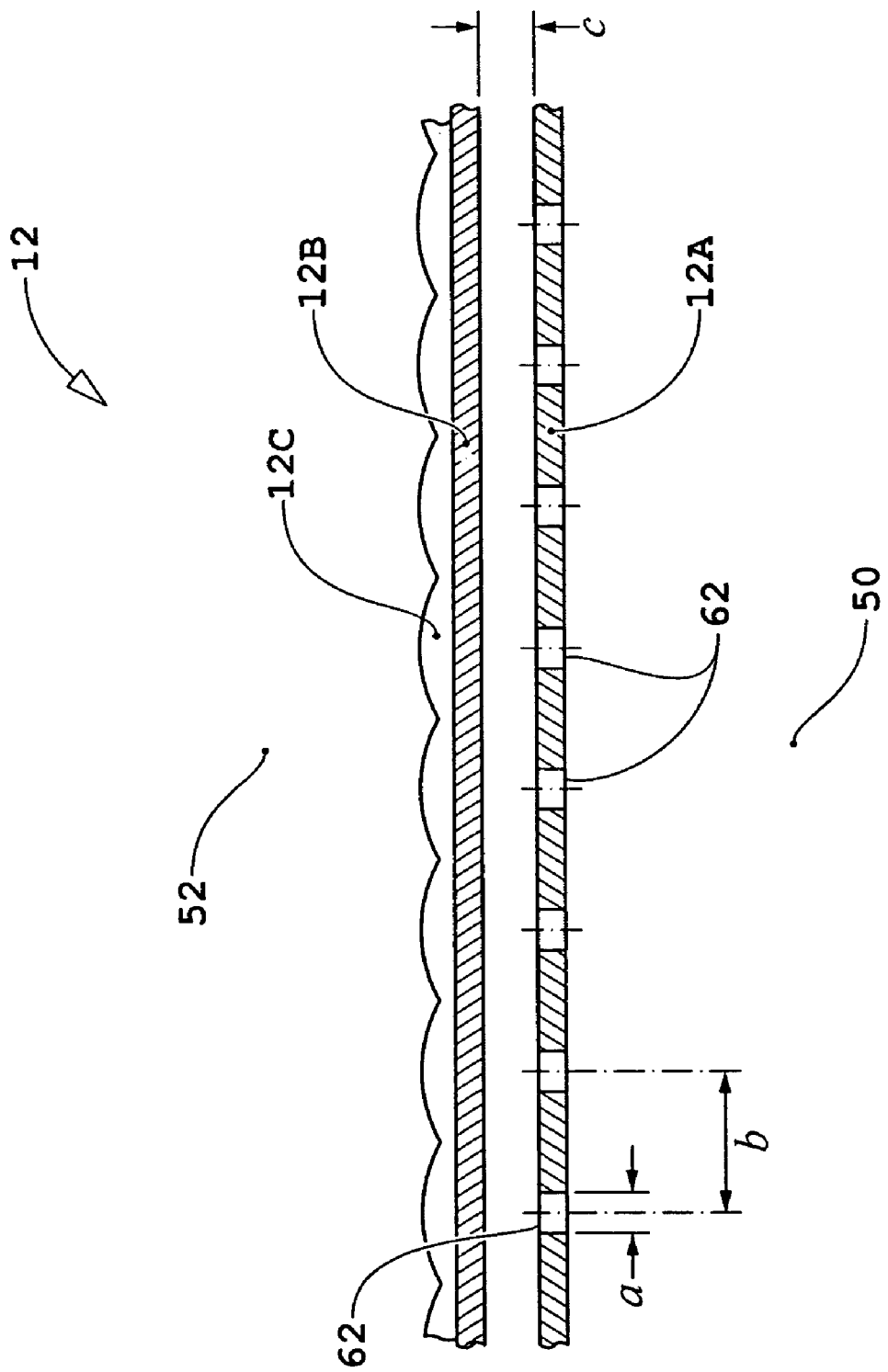
FIG. 1h is a schematic diagram of an array of microlenses placed behind a thin fluorescent layer and array of pinholes.

A second variant of interface 12 shown schematically in FIG. 1h in which no reduction of effects of off-axis aberrations is made. Interface 12 is formed by an array of microlenses 12C placed behind the thin fluorescent layer 12B and array of pinholes 12A of the first variant. The addition of the array of microlenses 12C reduces the numerical aperture required for the second imaging system 10B to obtain a given detection efficiency for beams transmitted by pinhole array 12A or increases the detection efficiency for a given numerical aperture of the second imaging system 10B.

The advantage of thin fluorescent spots of the first embodiment is that the fluorescent medium itself is used to define the boundary of a region to be used in generating the optical interference signal with a reduced background contribution, i.e., only short wavelength light that is incident on the fluorescent spot can contribute to the generation of the optical interference signal. When an opaque screen with apertures is used to define the light to be subsequently detected, a portion of the light that is transmitted by the opaque region of the screen outside of the apertures will also be detected. This particular source of background contributions is not present when using thin fluorescent spots.

The manufacture of an array of thin fluorescent spots can be done using microlithography techniques. The description of the manufacturing of the array of thin fluorescent spots is the same as the corresponding portion of the subsequent description given in with respect to the third variant of the first embodiment for the manufacture of thin fluorescent spots configured with a filled cone structure.

In a third variant of interface 12 of the first embodiment, no reduction of effects of off-axis aberrations is made and interface 12 is formed of an array of thin fluorescent spots wherein each spot comprises a filled cone structure to improve the detection efficiency over that of the first embodiment. An example of a cone structure fluorescent spot is shown schematically as element 1014A in Step 6 of FIG. 1i wherein element 1012A is an absorber, e.g., aluminum or platinum. The description of the size and spacing of the cone structures is the same as the corresponding portion of the description of the size a and spacing b of the apertures in interface 12 of the first embodiment of the present invention. The fluorescent spots in interface 12 may also comprise filled vee groove structures to enhance detection efficiency depending on the distribution of the measurement beam spots being imaged on interface 12.

Figure 1I:
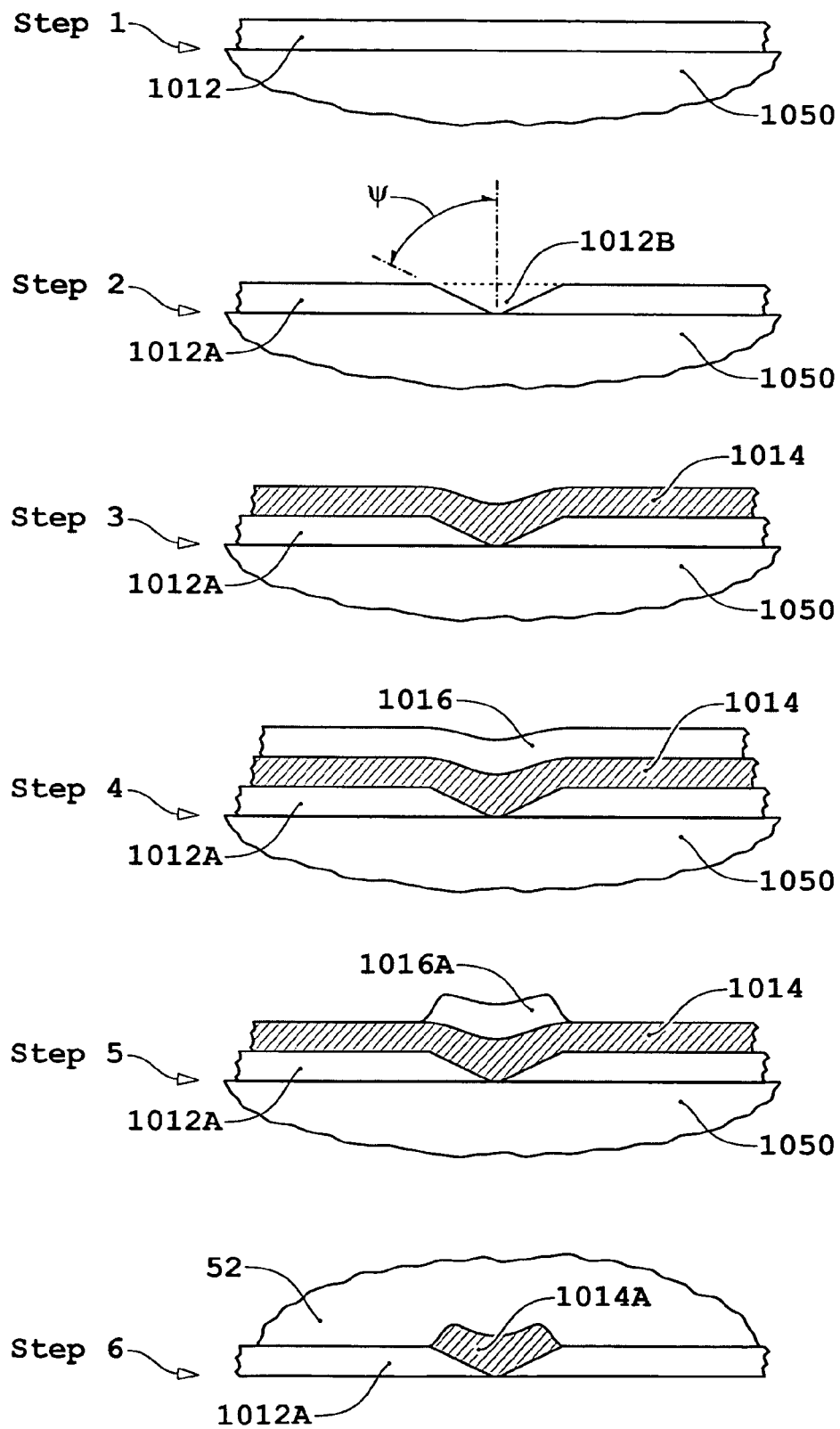
FIG. 1i is a schematic diagram of the lithography steps used in the manufacture of an array of thin fluorescent spots comprising a filled cone or vee groove structure.

The steps used in the manufacture of the array of thin fluorescent spots in the third variant are set out in FIG. 1i wherein the interface 12 is formed of an array of thin fluorescent spots comprising filled cone or vee groove structures. In step 1, the plane surface of a substrate 1050 is first coated with a release agent and then coated with a thin absorbing layer 1012, e.g., aluminum or platinum. The absorber medium is selected based on consideration of the reflectivity and absorption coefficient of the absorber medium at the wavelength radiated by the fluorescent medium and at the wavelengths used in imaging system 10A, respectively. The thickness of thin absorbing layer 1012 is of the order of 10 or more thicknesses of the absorber that attenuates a beam by a factor of 1/e at the wavelength used in imaging system 10A. In step 2, thin absorbing layer 1012 is etched to form absorbing layer 1012A with a focused ion beam (FIB) to generate the cone or vee groove shaped aperture 1012B. A typical half angle $\psi$ of the cone or vee groove structure (see Step 2 of FIG. 1i) is 60 or 70 degrees that corresponds to numerical apertures of 0.866 and 0.940, respectively.

The half angle $\psi$ is selected such that a portion of the fluorescent light radiated by the fluorescent spot 1014A outside of the numerical aperture of the second imaging system 10B is reflected/scattered into the numerical aperture of the second imaging system 10B so as to effectively increase the detection efficiency for short wavelength light incident on the fluorescent spot 1014A without degrading significantly the resolution of the second imaging system 10B. The choice of thickness of thin absorbing layer 1012 is also based on consideration of the thickness that will contribute to generation of an increased detection efficiency. The thickness may be for example 0.5 or 1 micron. The detection efficiency can be increased by a factor of $\leq 4$ over that obtained in the first embodiment of the present invention. A typical magnitude of the degrading of the resolution of the second imaging system 10B is of the order of 20%.

Continuing with the description of the Steps of FIG. 1i, absorbing layer 1012A and the array of filled cone or vee groove shaped apertures 1012B are coated in Step 3 with a thin fluorescent layer 1014, e.g., lumogen. In Step 4 of FIG. 1i, thin fluorescent layer 1014 is coated with a thin layer of a negative photoresist 1016. In Step 5, photoresist layer 1016 is patterned by either contact printing or by a lithography tool, developed, and the unexposed portion of layer 1016 dissolved leaving photoresist spots 1016A. In Step 6, the substrate comprising photoresist spots 1016A and thin fluorescent layer 1014 are etched so as to remove the thin fluorescent media not covered by the photoresist spots 1016A leaving thin fluorescent spots 1014A caped with photoresist spots. The photoresist caps may be removed as shown in Step 6 of FIG. 1i. The substrate comprising the array of thin fluorescent spots 1014A with or without the photoresist spots (the photoresist spots are removed if not transparent at the wavelength of the radiation emitted by the fluorescent spots 1014A) is bonded to convex lens 52 and lifted off of or separated from substrate 1050. In lieu of using a release agent, substrate 1050 may alternatively be removed by etching.

The advantage of thin fluorescent spots configured as filled cones or vee grooves shaped structures is that the fluorescent medium itself is used to help define the boundary of a region to be used in generating the optical interference signal, used to improve detection efficiency, and to reduce background contributions, i.e., only short wavelength light that is incident on the fluorescent spot can contribute to the generation of the optical interference signal. When an opaque screen with apertures is used to define the light to be subsequently detected, a portion of the light that is transmitted by the opaque region of the screen outside of the apertures will also be detected. This particular source of background contributions is not present when using thin fluorescent spots configured as cones or vee grooves.

Figure 1J:
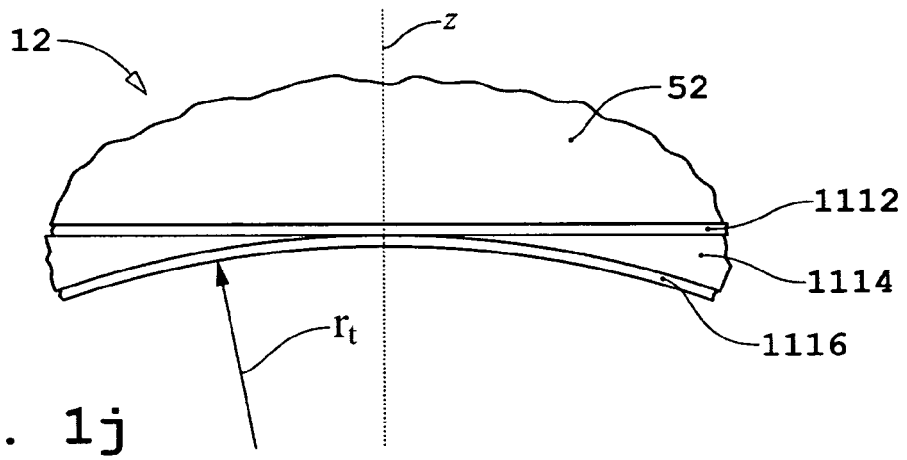
FIG. 1j is a schematic diagram of interface 12 wherein effects of off-axis aberrations are reduced.

The effects of off-axis aberrations are reduced in a fourth variant of interface 12 of the first embodiment shown schematically in FIG. 1*j*. Since the roles of object and image space of an imaging system are interchangeable, the fourth variant of interface 12 with the thin fluorescent medium omitted may be used in the object space of a catoptric or catadioptric imaging system to generate a diffraction limited spot on substrate 60 such as used in a confocal microscopy system or the fourth variant or interface 12 may be used in the image space of a catoptric or catadioptric imaging system to obtain diffraction limited information about a spot on substrate 60. Thus the description of only one of these two functions or roles for the fourth variant of interface 12 need be presented herein for description of either of the two applications. The use of of the fourth variant of interface 12 with the thin fluorescent medium omitted is further described with respect to FIG. 1*p*.

Figure 1K:
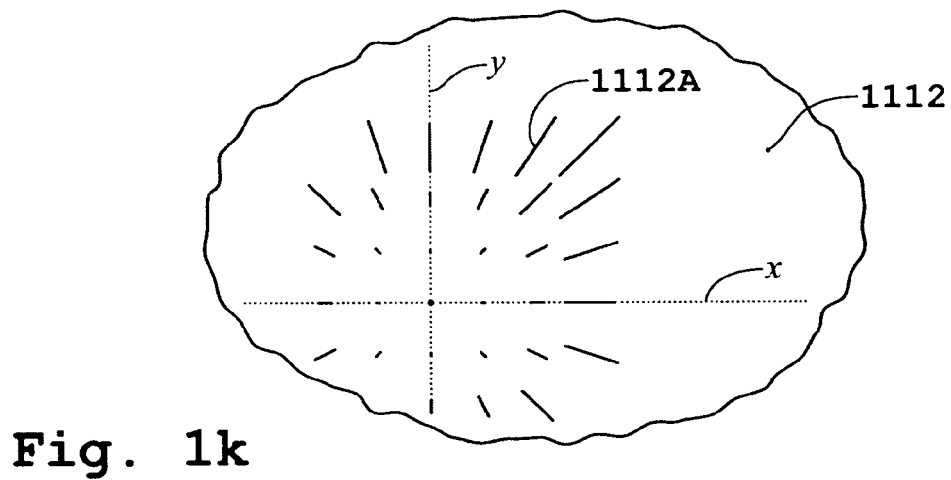
FIG. 1k is a schematic diagram of a sagittal plane absorbing layer comprising an array of sagittal slits.
Figure 1L:
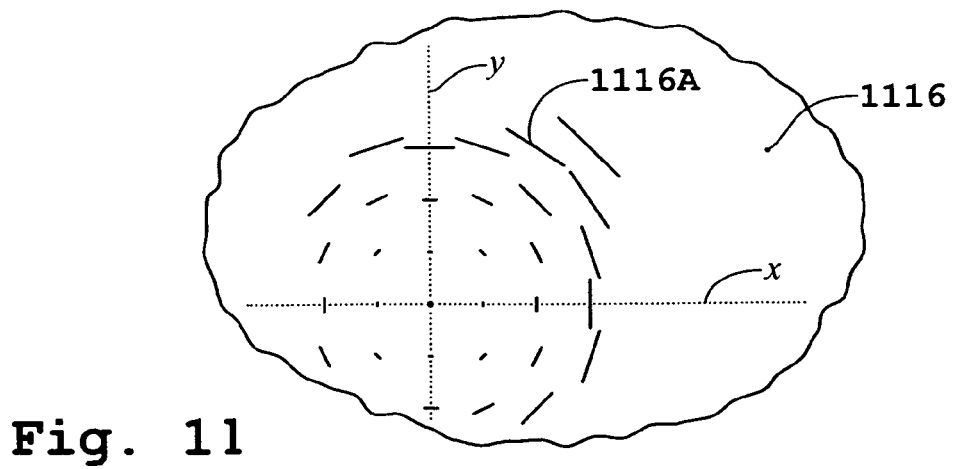
FIG. 1l is a schematic diagram of a concave tangential plane absorbing layer comprising an array of tangential slits.

The fourth variant of interface 12 comprises a plane absorbing layer 1112, a second absorbing concave layer 1116, and a transmitting layer 1114. Absorbing layers 1112 and 1116 coincide with the sagittal and tangential image surfaces, respectively, of catoptric imaging system 10A. Absorbing layers 1112 and 1116 further comprise arrays of sagittal slits 1112A and tangential slits 1116A, respectively, shown in FIGS. 1*k* and 1*l*, respectively.

For each slit of the array of sagittal slits, there is a corresponding slit of the array of tangential slits wherein corresponding sagittal and tangential slits are orthogonal with respect to each other and are conjugate images of a spot in the object space of catoptric imaging system 10A. In addition, the direction of the slits of the array of sagittal slits is toward the optic axis of the catoptric imaging system 10A corresponding to the origin of the coordinate system shown in FIG. 1*k*. Accordingly, the directions of the slits of the array of tangential slits are in respective azimuthal directions. Each of the sagittal slits is generated in the form of vee shaped groove facing convex lens 52 and comprising a thin fluorescent medium.

The radius of curvature of the concave surface is selected to match the radius of curvature $r_t$ of the tangential surface of imaging system 10A. Radius of curvature $r_t$ is related to $r_0$ given by the formula $$r_t = \frac{r_0}{2} \qquad (16)$$

where $r_0$ is the radius of curvature of a respective catoptric surface of imaging system 10A.

The first step in the construction of interface 12 of the fourth variant starts with the construction of an array of sagittal slits comprising elongated fluorescent spots. The description of the manufacturing steps for fabricating the array of sagittal slits 1112A comprising elongated fluorescent spots is the same as corresponding portions of the description given for the fabrication of the array of fluorescent spots of the third variant of the first embodiment. The length of the sagittal slits $l_s$ is the greater of a minimum value or a length $\Delta r$ determined by the NA of the imaging system and the separation between the sagittal and tangential surfaces $\Delta z$ at the radial position $\rho$ in the sagittal field. The minimum value may be less than or approximately equal to the resolution of imaging system 10A in the sagittal direction in certain end use applications or larger than the resolution in certain other end use applications such as described in cited U.S. Provisional Patent Application No. 60/485,507 (ZI-52) and U.S. patent application Ser. No. 10/765,229 (ZI-52). The length $\Delta r$ is given by the equation $$\Delta r = 2[\tan(\sin^{-1} NA)]\Delta z. \qquad (17)$$

The separation $\Delta z$ is given by the equation $$\Delta z = 2\frac{\rho^2}{r_0}. \qquad (18)$$

With the substitution of the expression for separation $\Delta z$ given by Eq. (18) into Eq. (17), the following expression for $\Delta r$ is obtained:

$$\Delta r = 4[\tan(\sin^{-1} NA)]\left(\frac{\rho^2}{r_0}\right). \qquad (19)$$

The second step in the construction of interface 12 of the fourth variant is the deposition of transmitting layer 1114 (see FIG. 1*j*) on surface of absorbing layer 1112 that generates a concave surface. The radius of curvature of the concave surface is $r_t$ given by Eq. (16) and the thickness of layer 1114 is $\Delta z$ with the location of the zero value of the thickness corresponding to the optic axis of catoptric imaging system 10A. The medium of layer 1114 is selected to have a real part of the refractive index $n \cong 1$ and a low value for the extinction coefficient or complex value $\kappa$ of the index of refraction. An example of a medium for the layer 1114 is silicon for wavelength $\leq 30$ nm with a NA $\leq 0.9$.

The thickness of the absorbing layer 1112 comprising for example media such as aluminum, platinum, rhodium, molybdenum, gold, iridium, tungsten, and silver is selected to furnish the attenuation of beams incident outside of the sagittal slits required by an end use application and in conjunction with respect to reflectivity at the radiated wavelength of the fluorescent medium to furnish the desired increase in detection efficiency by the use of fluorescent spots in the form of filled cones and vee grooves. The thickness of the absorbing layer 1116 also comprising for example media such as aluminum, platinum, rhodium, molybdenum, gold, iridium, tungsten, and silver is selected to furnish the attenuation of beams incident outside of the tangential slits required by an end use application. Accordingly, the thicknesses of absorbing layers 1112 and 1116 are of the order of 10 or more thicknesses of the absorber that attenuates a beam by a factor of 1/e at the wavelength used in imaging system 10A. The choice of thickness of thin absorbing layer 1112 is also based on consideration of the thickness that will contribute to generation of an increase in detection efficiency. The thicknesses may be for example 0.5 or 1 micron.

The third step in the construction of interface 12 of the fourth variant is the generation of the tangential slits in absorbing layer 1116. The shape of the tangential slits are vee shaped trenches or grooves with a typical half angle of the vee shaped trench or groove structure (see Step 2 of FIG. 1i) that is greater than the angle that corresponds to the numerical aperture of imaging system 10A used in the tangential direction, i.e., a radial direction. The apexes of the vee shaped trenches or grooves are adjacent to separating structure 1114. The length of the tangential slits $l_t$ is determined as the larger of a minimum value and $\Delta r$ determined by the NA of the imaging system and the separation between the sagittal and tangential surfaces $\Delta z$ at the radial position $\rho$ in the sagittal field and is given by the Eqs. (17) and (19). The minimum value may be less than or approximately equal to the resolution of imaging system 10A in the tangential direction in certain end use applications or larger than the resolution in the tangential direction in certain other end use applications such as described in cited U.S. Provisional Patent Application No. 60/485,507 (ZI-52) and U.S. patent application Ser. No. 10/765,229 (ZI-52).

The width of the vee shaped tangential grooves at the apex of the grooves may be less than or approximately equal to the resolution of imaging system 10A in tangential direction in certain end use applications or larger than the resolution in certain other end use applications such as described in cited U.S. Provisional Patent Application No. 60/485,507 (ZI-52) and U.S. patent application Ser. No. 10/765,229 (ZI-52).

It is apparent that the optical beam transmitted by the each corresponding set of sagittal and tangential slits is equivalent to the optical beam transmitted by a pinhole aperture placed in the field of diffraction limited images. Thus the optical interference signal generated by the thin fluorescent spots in the form of filled cones and vee grooves will be equivalent to the optical interference signal generated by the detection of light transmitted by a pinhole aperture placed in the field of diffraction limited images.

The value of the extinction coefficient $\kappa$ of the transmitting layer 1114 will determine in part the effective radius of the field of view that can be used to obtain diffraction limited information. The amplitude of the optical interference signal will be attenuated by the average of the factor $\exp(-2\alpha\Delta z)$ where $$\alpha\Delta z = (\sec \theta) k \kappa \Delta z, \qquad (20)$$

$\theta$ is the angle of refraction in transmitting layer 1114, and k is the wavenumber of the measurement and reference beams. Consider for example the effective radius of the field of view being defined by a maximum usable value for $\Delta z$, $\Delta z_m$, specified by the condition $\alpha\Delta z_m = 1$ for the maximum value of $\theta = \sin^{-1}(NA)$. The effective radius $\rho_m$ of the field of view is thus obtained for this definition through the combination of Eqs. (18) and (20) with the result $$\rho_m = \left[\frac{\lambda r_0 \cos(\sin^{-1} NA)}{4\pi\kappa}\right]^{1/2}. \qquad (21)$$

For an examples of $\kappa=0.01$ and 0.001, $r_0=50$ mm, $\lambda=30$ nm, and NA=0.9, the corresponding effective radius of the field of view is $\rho_m=77$ microns and $\rho_m=240$ microns, respectively.

Catoptric imaging system 10A of the first embodiment in general generates diffraction limited information for a larger NA compared for example to a 10× Schwarzshild Microscope [see the description of the Schwarzschild Microscope in *Lens Design Fundamentals* by R. Kingslake (Academic Press 1978)] by a factor of $\gtrsim 2$; has higher resolution compared to the Schwarzshild Microscope as a result of the larger NA; has a larger field of view compared to the Schwarzshild Microscope; and has no large central obscuration as compared to the Schwarzshild Microscope which has radius equal to approximately ½ of the radius of the cone defined by the corresponding NA.

Figure 1M:
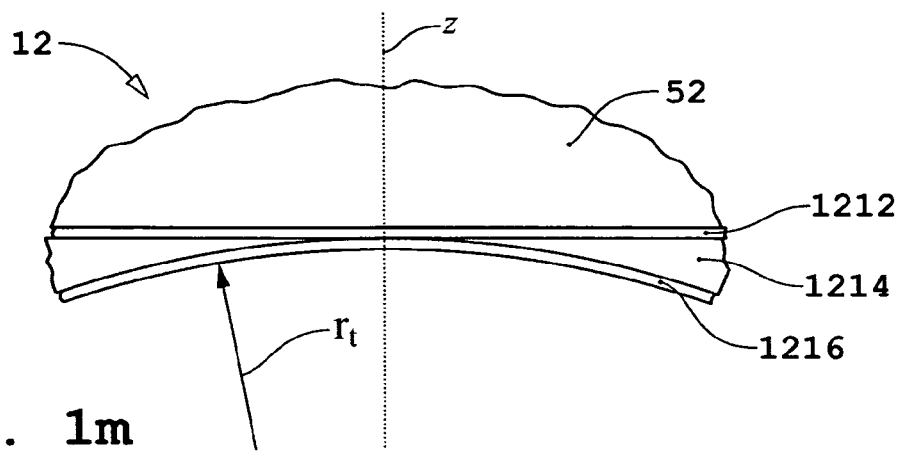
FIG. 1m is a schematic diagram of interface 12 wherein effects of off-axis aberrations are reduced.

In a fifth variant of interface 12 of the first embodiment shown schematically in FIG. 1m, effects of off-axis aberrations are reduced. As with the fourth variant of interface 12, the fifth variant of interface 12 with the thin fluorescent medium omitted may be used in the object space of a catoptric or catadioptric imaging system to generate a diffraction limited spot on substrate 60 such as used in a confocal microscopy system or the fifth variant of interface 12 may be used in the image space of a catoptric or catadioptric imaging system to obtain diffraction limited information about a spot on substrate 60. Thus the description of only one of these two functions or roles for the fifth variant of interface 12 need be presented herein for description of either of the two applications. The use of fifth variant of interface 12 with the thin fluorescent medium omitted is further described with respect to FIG. 1p.

Figure 1N:
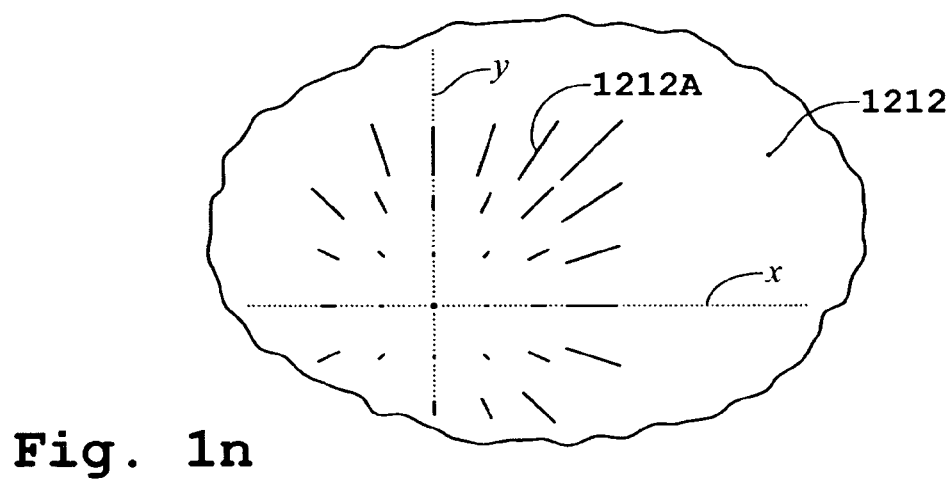
FIG. 1n is a schematic diagram of a sagittal plane absorbing layer comprising an array of sagittal slits.
Figure 1O:
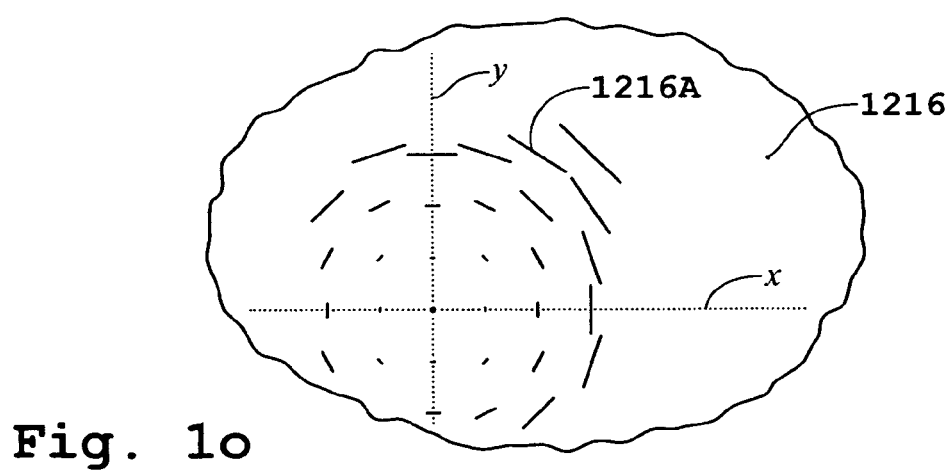
FIG. 1o is a schematic diagram of a concave tangential plane absorbing layer comprising an array of tangential slits.

The fifth variant of interface 12 comprises a first array of sagittal slits 1212A in a plane absorbing layer 1212 shown in FIG. 1n, a second array of tangential slits 1216A in a concave absorbing layer 1216 shown in FIG. 1o, and a separating structure 1214 comprising an array of apertures. For each slit 1212A of the first array of sagittal slits, there is a corresponding tangential slit 1216A of the second array of slits and a corresponding aperture of separating structure 1214 wherein corresponding slits are orthogonal with respect to each other and are conjugate images of a spot in the object space of catoptric imaging system 10A. In addition, the directions of the slits of the sagittal array of slits are toward the optic axis of the catoptric imaging system 10A. Accordingly, the directions of the slits of the tangential array of slits are in respective azimuthal directions. Each of the sagittal slits 1212A is generated in the form of vee shaped groove facing convex lens 52 and comprising a thin fluorescent medium.

The radius of curvature of the concave layer 1216 is selected to match the radius of curvature $r_t$ of the tangential surface of imaging system 10A given by Eq. (16).

The first step in the construction of interface 12 of the fifth variant starts with the construction of an array of sagittal slits 1212A comprising elongated fluorescent spots in the form of filled vee grooves. The description of the manufacturing steps for fabricating the array of sagittal slits 1212A comprising the elongated fluorescent spots is the same as corresponding portions of the description given for the fabrication of the array of fluorescent spots of the third and fourth variants of the first embodiment. The length of the sagittal slits $l_s$ is determined as the larger of a minimum value and $\Delta r$ determined by the NA of the imaging system and the separation between the sagittal and tangential surfaces $\Delta z$ at the radial position $\rho$ in the sagittal field and is given by the Eqs. (17) and (19). The minimum value may be less than or approximately equal to the resolution of imaging system 10A in the sagittal direction in certain end use applications or larger than the resolution in the sagittal direction in certain other end use applications such as described in cited U.S. Provisional Patent Application No. 60/485,507 (ZI-52) and U.S. patent application Ser. No. 10/765,229 (ZI-52).

The thickness of the absorbing layer 1212 comprising for example media such as aluminum, platinum, rhodium, molybdenum, gold, iridium, tungsten, and silver is selected to furnish the attenuation of beams incident outside of the sagittal slits required by an end use application and in conjunction with respect to reflectivity at the radiated wavelength of the fluorescent medium to furnish the desired increase in detection efficiency by the use of fluorescent spots in the form of filled cones and vee grooves. Accordingly, the thicknesses of absorbing layer is of the order of 10 or more thicknesses of the absorber that attenuates a beam by a factor of 1/e at the wavelength used in imaging system 10A.

The width of the vee shaped grooves at the apex of the grooves may be less than or approximately equal to the resolution of imaging system 10A in sagittal direction in certain end use applications or larger than the resolution in certain other end use applications such as described in cited U.S. Provisional Patent Application No. 60/485,507 (ZI-52) and U.S. patent application Ser. No. 10/765,229 (ZI-52).

The second step in the construction of interface 12 of the fifth variant is the deposition of separating structure 1214 (see FIG. 1m) on surface of absorbing layer 1212 that generates a concave surface. The radius of curvature of the concave surface is $r_t$ given by Eq. (16) and the thickness of separating structure 1214 is $\Delta z$ given by Eq. (18) with the location of the zero value of the thickness corresponding to the optic axis of catoptric imaging system 10A. The medium of separating structure 1214 is selected according to considerations of ease of deposition, to ease of generating the concave surface, to ease of etching the corresponding apertures, and to a low reflectivity for the wavelengths to be used in the first embodiment. The selection of a medium with a low reflectivity leads to a reduction of background generation that results from background beams being reflected by the surfaces of the cone and vee grooves into the imaging system 10B. An example of a medium with a low reflectivity at a wavelength of 30 nm is Si.

The separating structure 1214 may comprise two layers with a first thin layer that may serve as a stop layer in the etching and/or polishing of separating structure 1214 and to serve as layer to protect the array of sagittal slits 1212A in layer 1212 comprising vee grooves filled by a fluorescent media. The stop layer may be selected based on etching sensitivities or based on use as a tag which indicates when the stop layer has been reached in an etching process. An example of a stop layer is Ru.

Concave surface of separating structure 1214 may be generated during the process of deposition such as evaporation. A final figuring of concave surface of separation layer 1214 may be done using ion milling. The apertures of the array of apertures in separating structure 1214 are generated for example by ion milling with a FIB. The apertures of the array of apertures may be nominally square or circular in cross-section with a diagonal length or diameter, respectively, greater than or equal to length $l_s$. The apertures of the array of apertures may also be generated as vee shaped grooves with the apex of the vee shaped grooves adjacent to and aligned with the direction of the sagittal slits of plane absorbing layer 1212. A typical half angle of the vee trench or groove structure (see Step 2 of FIG. 1i) is greater than the angle that corresponds to the numerical aperture of imaging system 10A used in the sagittal direction, i.e., an azimuthal direction.

The third step in the construction of interface 12 of the fifth variant is the generation of concave absorbing layer 1216 (see FIG. 1m) on surface of separating structure 1214 that generates a concave surface. Concave absorbing layer 1216 is generated as a self supporting concave structure that has a radius of curvature $\leq 0.9 r_t$. The self supporting concave structure is fabricated by a multistep process utilizing the membrane technology developed for X-ray mask fabrication such as described in articles by T. Haga, M. C. K. Tinone, M. Shimada, T. Ohkubo, and A. Ozawa entitled "Soft X-ray multilayer beam splitters," *J. Synchrotron Rad.* 5, p. 690 (1998) and by T. Haga, M. C. K. Tinone, M. Shimada, T. Ohkubo, and A. Ozawa, *Proc. SPIE* 2873, p 105 (1996) for which the contents of each of the two articles are incorporated herein their entirety by reference.

In the work described in cited articles by Haga et al., precise control of multilayer stress is used to obtain fabrication of a large and flat reflection surface in beam-splitters. The measured flatness of the beam-splitters was better than 5 nm (rms) in all cases and the best case had a flatness was 1.1 nm (rms) in a central area of 7 mm by 7 mm. The internal stress is controlled using techniques such as described in cited articles by Haga et al., to generate a self supporting concave absorbing layer that has the prescribed radius of curvature.

The fourth step in the construction of interface 12 of the fifth variant is the attachment of the self supporting concave absorbing layer generated in the third step to separating structure 1214 at the edges of the field of view to form concave absorbing layer 1216. Since the radius of curvature of the self supporting concave absorbing layer generated in the third step is less than the corresponding radius of curvature of separating structure 1214, the final shape of the formed concave absorbing layer 1216 is determined by the radius of curvature of separating structure 1214. The thickness of the absorbing layer 1216 is selected to furnish the attenuation of beams incident outside of the tangential slits subsequently formed required by an end use application. Accordingly, the thicknesses of absorbing layer 1216 is of the order of 10 or more thicknesses of the absorber that attenuates a beam by a factor of 1/e at the wavelength used in imaging system 10A.

The fifth step in the construction of interface 12 of the fifth variant is the generation of the tangential slits in absorbing layer 1216. The shape of the tangential slits are vee shaped trenches or grooves with a typical half angle of the vee shaped trench or groove structure (see Step 2 of FIG. 1i) that is greater than the angle that corresponds to the numerical aperture of imaging system 10A used in the tangential direction, i.e., a radial direction. The apexes of the vee shaped trenches or grooves are adjacent to separating structure 1214. The length of the tangential slits $l_s$ is determined as the larger of a minimum value and $\Delta r$ determined by the NA of the imaging system and the separation between the sagittal and tangential surfaces $\Delta z$ at the radial position $\rho$ in the sagittal field and is given by the Eqs. (17) and (19). The minimum value may be less than or approximately equal to the resolution of imaging system 10A in the tangential direction in certain end use applications or larger than the resolution in the tangential direction in certain other end use applications such as described in cited U.S. Provisional Patent Application No. 60/485,507 (ZI-52) and U.S. patent application Ser. No. 10/765,229 (ZI-52).

The width of the vee shaped tangential grooves at the apex of the grooves may be less than or approximately equal to the resolution of imaging system 10A in tangential direction in certain end use applications or larger than the resolution in certain other end use applications such as described in cited U.S. Provisional Patent Application No. 60/485,507 (ZI-52) and U.S. patent application Ser. No. 10/765,229 (ZI-52).

An advantage of the first embodiment of the present invention and variants thereof of interface 12 is that interferometer system 10 is achromatic over the range from the IR to the EUV and that with the generation of the optical interference signal in the intensity of beam 34, the specifications of the second imaging system 10B are further relaxed as compared when the second imaging system 10B must preserve the phase relationship between reference and measurement beam components.

A variant of catoptric imaging system 10A of the first embodiment and variants thereof of interface 12 is shown schematically in FIG. 1e as catoptric imaging system 1410A. Catoptric imaging system 1410A is the same as catoptric imaging system 10A of the first embodiment and variants thereof of interface 12 except that the nominal radii of curvature for the adaptive reflective surfaces of catoptric imaging system 1410A corresponding to the first, second, third, and fourth single concave reflecting surfaces of the first embodiment and variants thereof of are all equal. The remaining description of the variant of catoptric imaging system 1410A is the same as the corresponding portion of the descriptions given for catoptric imaging system 10A of the first embodiment and variants thereof of.

Imaging Systems Used As A Projection Optic

Figure 1P:
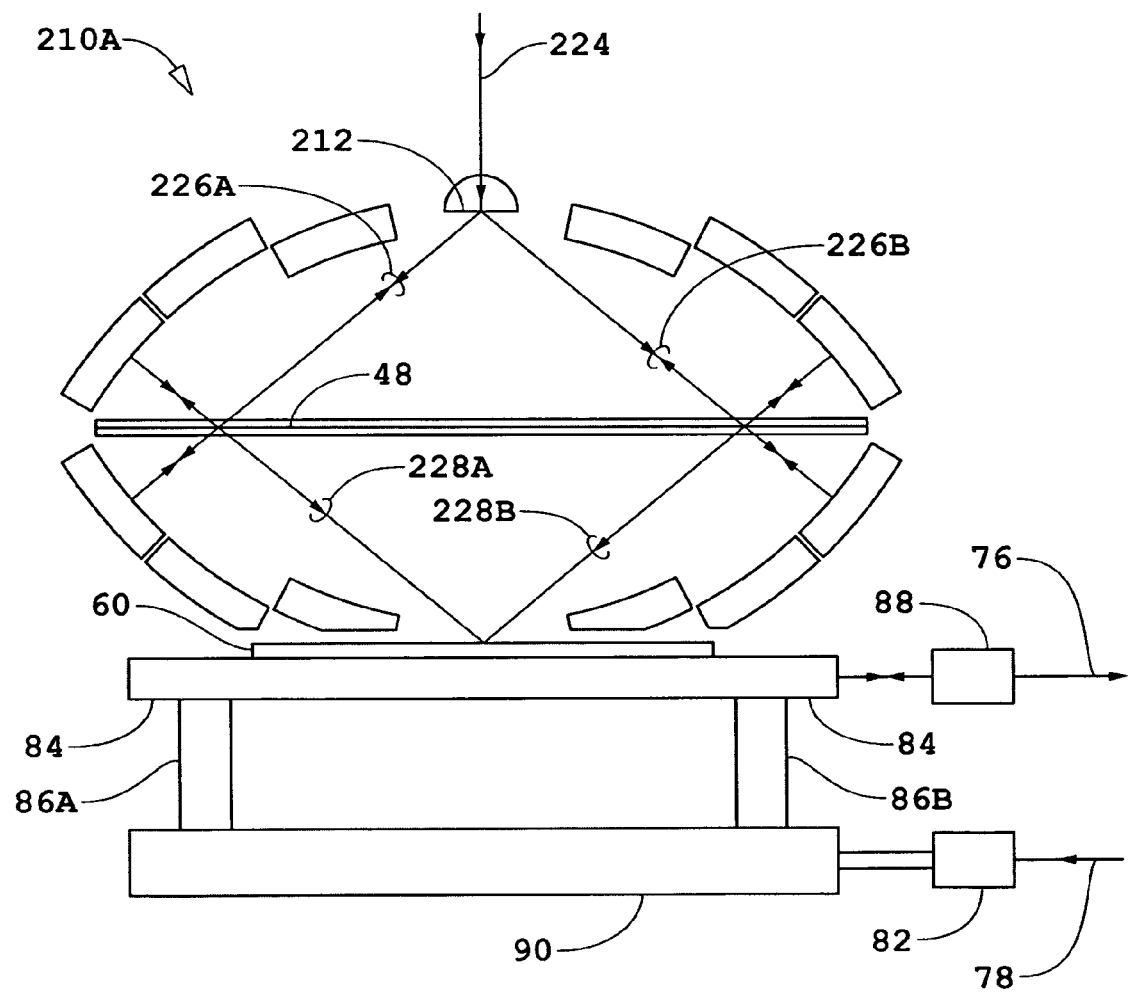
FIG. 1p is a schematic diagram of a catoptric imaging system used as a projection optic.

A catoptric imaging system 210A is shown in FIG. 1p where it is used as a projection optic with effects of off-axis and/or on-axis aberrations reduced to generate diffraction limited spots on substrate 60. Catoptric imaging system 210A may be used as the source section of a confocal interferometric imaging system to illuminate a substrate 60 or to write information onto substrate 60 coated for example with photoresist. The descriptions of the elements in FIG. 1p that have the same numerals as elements in FIG. 1b are the same as the descriptions given for the same numeral elements in FIG. 1b.

When catoptric imaging system 210A is used as the source section of a confocal interferometric imaging system, input beam 224 is the same as input beam 24C shown in FIG. 1b. When catoptric imaging system 210A is used to write information onto substrate 60 coated for example with photoresist, input beam 224 corresponds to a beam configured for example as an exposure beam of a lithography tool.

Interface 212 is the same an as either the fourth or fifth variants of interface 12 shown in FIGS. 1j–1l and FIGS. 1m–1o, respectively, with the omission of the fluorescent medium. Since the roles of object and image space of an imaging system are interchangeable, the descriptions of beams 226A, 226B, 228A and 228B in FIG. 1p are the same as the descriptions given for beams 26A, 26B, 28A and 28B, respectively, in FIG. 1b except that the directions of propagation of corresponding beams are reversed.

Imaging system 210A may alternatively comprise a catadioptric imaging system or an imaging system having only transmitting elements without departing from the scope and spirit of the invention.

Catoptric Imaging Systems Comprising A Thin Beam-Splitter

The first embodiment of the present invention comprises a thin beam-splitter 48. Thin beam-splitter 48 may comprise a self supporting a stack of one or more thin layers of refractive media, may comprise a thin reflective layer or stack of layers with an array of transmitting apertures wherein the size of the apertures is larger than the wavelength of an optical beam being focused by the imaging system, or may comprise an array or grid of conducting wires.

Self supporting beam-splitter 48 is fabricated by a multistep process utilizing the membrane technology developed for X-ray mask fabrication such as described in cited articles by T. Haga, M. C. K. Tinone, M. Shimada, T. Ohkubo, and A. Ozawa. The residual on-axis optical aberrations introduced by the finite thickness of thin self supporting beam-splitter 48 and departures of thin beam-splitter 48 from uniform thickness and flatness may be compensated in part in catoptric imaging system 10A by modifying the shapes and adjusting the positions and locations of the adaptive reflective surfaces 42A-1, 42A-2, 42A-3, 42C-1, 42C-2, 42C-3, 46A-1, 46A-2, 46A-3, 46C-1, 46C-2, and 46C-3 (see FIG. 1c).

Thin self supporting beam-splitter 48 is shown as lying in a horizontal plane in the FIGS. 1b–1f of first embodiment. However, the effect of the earths' gravitational field may introduce an unacceptable level of the sag in the pellicles and accordingly, the orientation of the pellicles will preferably be in a vertical plane. Beam-splitter 48 may also be supported against gravitational effects by a matrix of radial ribs (not shown in figure) that are designed to obstruct a minimum of the clear aperture of imaging system 10A. The matrix of radial ribs may be fabricated from a silicon wafer using microlithography techniques or MEMS techniques.

The use of beam-splitter 48 fabricated for operation in the UV to EUV and/or in the IR permit operation of the catoptric imaging system 10A in the respective wavelength domains. A catoptric grade beam-splitter may be produced as an array of apertures in a reflecting self supporting layer of one or more refractive media. The radian and azimuthal dimensions $\Delta r$ and $w$, respectively, of the apertures corresponding to an angle of incidence $\theta$ of a beam at the beam-splitter and generated by an on-axis source and corresponding to an adaptive reflective surface is selected such that $$\lambda \Delta x \geq 3(\Delta r \cos \theta)^2, \qquad (22)$$

$$\lambda \Delta x \geq 3 w^2, \qquad (23)$$

where $\Delta x$ is a weighted average path length of measurement and/or reference beams for the adaptive reflective surface, e.g., beams 26C, 26D, 28A, and 28B and adaptive reflective surfaces 42A-1, 42A-2, 42A-3, 42C-1, 42C-2, 42C-3, 46A-1, 46A-2, 46A-3, 46C-1, 46C-2, and 46C-3 shown in FIG. 1c. Note that the radial and azimuthal dimensions for the apertures of the aperture array will generally be different for optimum performance of the beam-splitter. In addition, the radial dimension of the apertures will generally be dependent on the angle of incidence $\theta$ of a beam, e.g., proportional to $\sec\theta$ [see Eq. (22)], for optimum performance of the beam-splitter. The operation with a catoptric grade beam-splitter 48 reduces the optical path lengths of measurement and reference beams in a refractive media to nominally zero.

Microlithography techniques or MEMS techniques can be used for the manufacture of beam-splitter 48 generated as an array of apertures in a self supporting pellicle that has reflective surfaces. The catoptric beam-splitter can also be manufactured as crossed arrays or grids of conducting wires such as applicable for longer wavelengths.

Another form of a catoptric imaging system that may be used for catoptric imaging system 10A is a variant of the catadioptric imaging system such as described in commonly owned U.S. Provisional Patent Application No. 60/460,129 (ZI-51) and U.S. patent application Ser. No. 10/816,172 (ZI-51) wherein both are entitled "Apparatus and Method for Measurement of Fields of Forward Scattered/Reflected and Backscattered Beams by an Object in Interferometry" and both are by Henry A. Hill, the contents of which are herein incorporated in their entirety by reference.

The remaining description of the embodiment of the present invention based on the variant of the catadioptric imaging system is the same as the corresponding portions of the descriptions of the first embodiment and variant thereof of interface 12 and of the catadioptric imaging systems given in cited U.S. Provisional Patent Applications No. 60/485,507 (ZI-52) and No. 60/485,255 (ZI-53) and U.S. patent application Ser. No. 10/765,229 (ZI-52) and Ser. No. 10/886,157 (ZI-53).

The mode of operation wherein the object plane is located in the interior of substrate 60 can be used to measure properties of unfilled and filled trenches and vias. The high speed vertical scanning mode makes it possible to measure the properties of the trenches and vias as a function of depth into substrate 60. The interior mode of operation may also be beneficially used in scanning for defects in trenches and vias that are either unfilled or filled with either a transparent dielectric or a conductor.

The second embodiment of the present invention comprises interferometer 10 and catoptric imaging system 10A of the first embodiment, variant thereof, and variants thereof of interface 12 except that interface 12 of the first embodiment, variant thereof, and variants thereof of interface 12 is replaced by an interface 12 which has the thin fluorescent spots or layers omitted. Interface 12 of the second embodiment functions as a pinhole array beam-splitter for generating the reference and measurement beams and for the function of combining the reference and measurement beam reflected/scattered by substrate 60 such as described in cited U.S. Provisional Patent Application No. 60/442,982 (ZI-45) and U.S. patent application Ser. No. 10/765,229 (ZI-45). The remaining description of the second embodiment is the same as corresponding portions of the first embodiment, variants thereof, and variants thereof of interface 12.

A general description of embodiments of the present invention shown diagrammatically in FIG. 2a will next be given for interferometer systems operating in a transmission mode. Much of the description given for the interferometer systems operating in the reflection mode is the same as the description for the interferometer systems operating in the transmission mode.

The embodiments of the present invention configured for operation in the transmission mode use either N-dimensional bi- or quad-homodyne detection methods for fields transmitted by substrate 60. When input beam 24 comprises coextensive reference and measurement beams, first and second portions of input beam 24 are reflected and transmitted, respectively, as measurement beam 324A and reference beam 324B, respectively, by non-polarizing beam-splitter 354A. When input beam 24 comprises non-coextensive reference and measurement beams, element 354A functions as mirror to reflect the measurement beam component of beam 24 as beam 324A leaving the reference beam component beam 24 as reference beam 324A. The description of input beam 24 is the same as the description given for the input beam 24 used in the embodiments of the present invention configured for operation in the reflection mode.

Figure 2A:
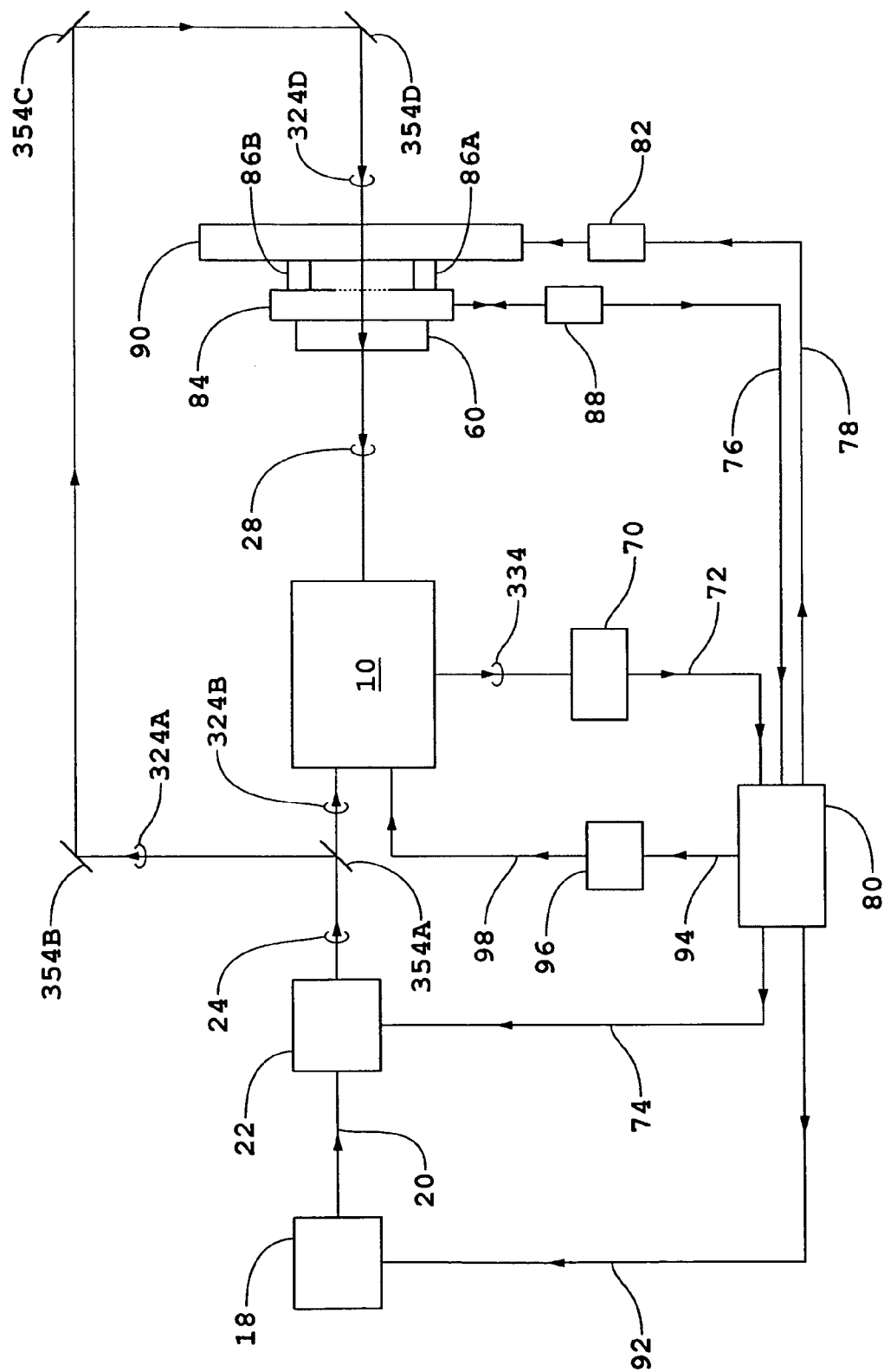
FIG. 2a is a schematic diagram of an interferometric non-confocal microscope system operating in a transmission mode.

Interferometer 10 of FIG. 2a comprises a catoptric imaging system that may have no adaptive reflecting surfaces or may have one or more adaptive reflecting surfaces. For the catoptric imaging systems that comprise one or more adaptive reflecting surfaces, the shapes of the one or more adaptive reflecting surfaces are controlled by a signal 98 from servo controller 96 according to error signal 94 from electronic processor and controller 80. The descriptions of signal 98, servo controller 96, and electronic processor and controller 80 is the same as corresponding portions of the description given for embodiments of the present invention configured for operation in the reflection mode.

A portion of measurement beam 324A is incident on the backside of substrate 60 as measurement beam 324D after reflection by mirror systems 354B, 354C, and 354D. Substrate 60 may comprise a reticle mask with or without a pellicle protective interface. If a pellicle protective interface is part of substrate 60, interferometer 10 may need to be configured for a large working distance, e.g., 6 mm. The working distance of interferometer 10 can be increased for example by removing a horizontal portion of the catoptric element adjacent to substrate 60 at the expense of increasing the size of the central obstruction presented to beams reflected/scattered or transmitted by the catoptric imaging system. A portion of measurement beam 324D incident on the backside of substrate 60 is transmitted as transmitted measurement beam 328. Measurement beam 328 and reference beam 324B are combined in interferometer 10 and exit as output beam 332. Output beam 332 is detected by detector 70 as electrical interference signal 72.

Figure 2B:
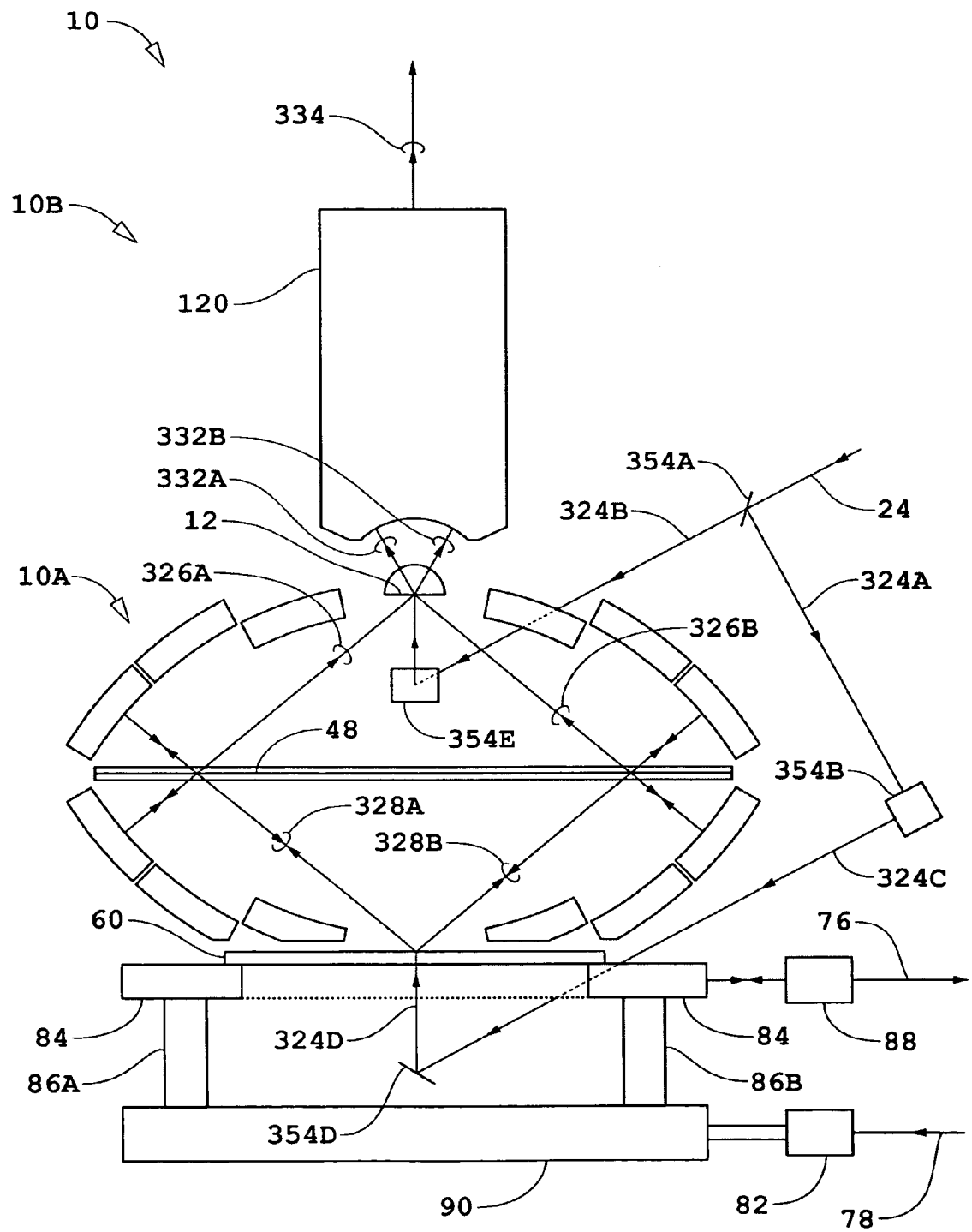
FIG. 2b is a schematic diagram of an interferometric non-confocal microscope system operating in a transmission mode that uses a catoptric imaging system comprising a pellicle beam-splitter and adaptive catoptric surfaces.

Interferometer 10 of the third embodiment of the present invention is shown schematically in FIG. 2b and comprises an interferometer operation in the transmission mode. Interferometer 10 of the third embodiment comprises a first imaging system generally indicated as numeral 10A, interface 12, and a second imaging system generally indicated as numeral 10B. The description of the first and second imaging systems 10A and 10B, respectively, is the same as the description of the first and second imaging systems 10A and 10B of the first embodiment, variant thereof, and variants thereof of interface 12 and of the second embodiment of the present invention.

The description of beams 332A, 332B, and 334 of the third embodiment is the same as the corresponding portion of the description given for beams 32A, 32B, and 34 of the first embodiment, variant thereof, and variants thereof of interface 12 and of the second embodiment. Also the description of beams 328A, 328B, 326A, and 326B of the third embodiment is the same as the corresponding portion of the description given for beams 28A, 28B, 26A, and 26B of the first embodiment, variant thereof, and variants thereof of interface 12 and of the second embodiment. The remaining description of the third embodiment is the same as corresponding portions of the descriptions given for the first embodiment, variant thereof, and variants thereof of interface 12 and the second embodiment of the present invention.

The Mirau interferometric microscope such as described in the article entitled "At-wavelength extreme ultraviolet lithography mask inspection using a Mirau interferometric microscope" by T. Haga, H. Takenaka, and M. Fukuda, *J. Vac. Sci. Technol. B*, 18, p 2916 (2000) may be used in other embodiments of the present invention as catoptric imaging 10A of the first embodiment, variant thereof, and variants thereof of interface 12 and second embodiment of the present invention. The Mirau interferometric microscope described by Haga et al. uses a Schwarzshild microscope.

Other embodiments of the present invention are generated with the omission of the fluorescent media of interface 12 of the variants of interface 12 on the present invention for operation in the IR and visible.

Additional other embodiments of the present invention are generated wherein the image space comprising interface 12 of the first embodiment and variant thereof, the second embodiment, and the third embodiment and variants thereof interface 12 with the fluorescent media omitted is used as the object space of a catoptric imaging system to produce a diffraction image in the respective image space.

Applications

The catoptric imaging systems described above can be especially useful in alignment mark identification on a stepper or scanner of lithography applications used for fabricating large scale integrated circuits such as computer chips and the like and in a stand-alone metrology system for measuring overlay performance of the stepper or scanner. The catoptric imaging systems described above can also be especially useful in inspection of masks used in the stepper or scanner and in the inspection of wafers at different stages of the fabrication of large-scale integrated circuits.

Lithography is the key technology driver for the semiconductor manufacturing industry. In particular, overlay improvement is one of the five most difficult challenges down to and below 100 nm line widths (design rules), see, for example, the *Semiconductor Industry Roadmap*, p 82 (1997). Since a lithography tool may produce $50–100 M/year of product, the economic value from improving (maintaining) performance of the lithography tool is substantial. Each 1% increase (loss) in yield of the lithography tool results in approximately $1 M/year economic benefit (loss) to the integrated circuit manufacturer and a substantial competitive advantage or disadvantage to the lithography tool vendor.

Overlay is measured by printing one pattern on one level of a wafer and a second pattern on a consecutive level of the wafer and then measuring, on a stand-alone metrology system, the difference in the position, orientation, and distortion of the two patterns.

A stand-alone metrology system for measuring overlay comprises a microscope system for viewing the patterns, such as the catoptric imaging systems described above, connected to laser gauge-controlled stage for measuring the relative positions of the patterns, and a wafer handling system.

The function of a lithography tool is to direct spatially patterned radiation onto a photoresist-coated wafer. The process involves determining which location of the wafer is to receive the radiation (alignment) and applying the radiation to the photoresist at that location.

To properly position the wafer, the wafer includes alignment marks on the wafer that can be measured by dedicated sensors such as the scanning interferometric near-field confocal systems described above. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the resist that convert the radiation pattern into a latent image within the resist.

When a mask is made, it must be perfect. Any defects in the pattern will destroy the functionality of the semiconductor circuit that is printed with that mask. Before a mask is delivered to the semiconductor manufacturing line, it is passed through an automated mask inspection system that searches for any defects in the pattern. There are two possible strategies in mask inspection, known as die-to-database and die-to-die inspection. The first method involves an automated scanning microscope that compares the mask pattern directly with the computer data used to generate the mask. This requires a very large data handling capability, similar to that needed by the mask writer itself. Any discrepancy between the inspected mask pattern and the data set used to create it is flagged as an error. The catoptric imaging systems described above are especially well suited for automated mask inspection with its advantages in background reduction and in the substantially simultaneous acquisition of one-dimensional line section images and two-dimensional section images.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithoography: Science and Technology* (Marcel Dekker, Inc., New York, 1998), the contents of which is incorporated herein by reference.

Figure 3A:
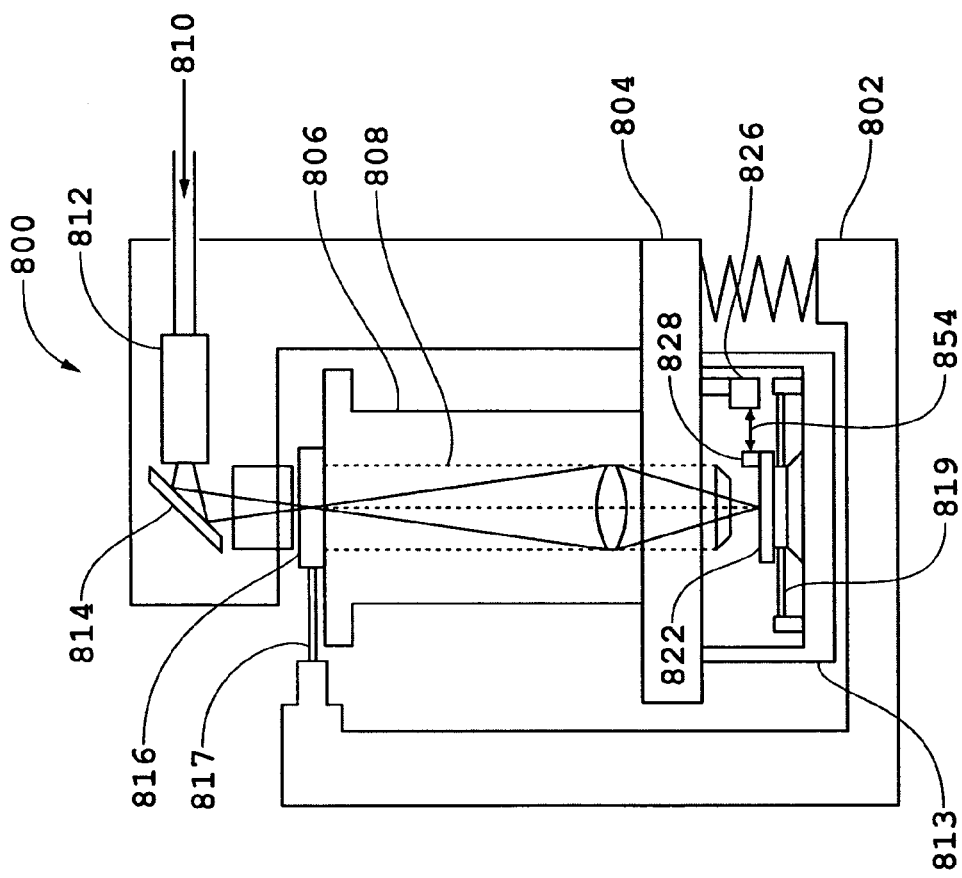
FIG. 3a is a schematic diagram of a lithography tool that uses catoptric imaging systems with pellicle or aperture array beam-splitters (not shown in figure).

An example of a lithography scanner 800 using a catoptric imaging system (not shown) is shown in FIG. 3a. The catoptric imaging system is used to precisely locate the position of alignment marks on the wafer (not shown) within an exposure system. Here, stage 822 is used to position and support the wafer relative to an exposure station. Scanner 800 includes a frame 802, which carries other support structures and various components carried on those structures. An exposure base 804 has mounted on top of it a lens housing 806 atop of which is mounted a reticle or mask stage 816, which is used to support a reticle or mask. A positioning system for positioning the mask relative to the exposure station is indicated schematically by element 817. Positioning system 817 can include, e.g., piezoelectric transducer elements and corresponding control electronics. Although, it is not included in this described embodiment, one or more interferometry systems are used to precisely measure the position of the mask stage as well as other moveable elements whose position must be accurately monitored in processes for fabricating lithographic structures (see supra Sheats and Smith *Microlithoeraphy: Science and Technology*).

Suspended below exposure base 804 is a support base 813 that carries wafer stage 822. Stage 822 includes a plane mirror 828 for reflecting a measurement beam 854 directed to the stage by interferometry system 826. A positioning system for positioning stage 822 relative to interferometry system 826 is indicated schematically by element 819. Positioning system 819 can include, e.g., piezoelectric transducer elements and corresponding control electronics. The measurement beam reflects back to the interferometry system, which is mounted on exposure base 804.

During operation, a radiation beam 810, e.g., an UV beam from a UV laser (not shown) passes through a beam shaping optics assembly 812 and travels downward after reflecting from mirror 814. Thereafter, the radiation beam passes through a mask (not shown) carried by mask stage 816 The mask (not shown) is imaged onto a wafer (not shown) on wafer stage 822 via a lens assembly 808 carried in a lens housing 806. Base 804 and the various components supported by it are isolated from environmental vibrations by a damping system depicted by spring 820.

Figure 3B:
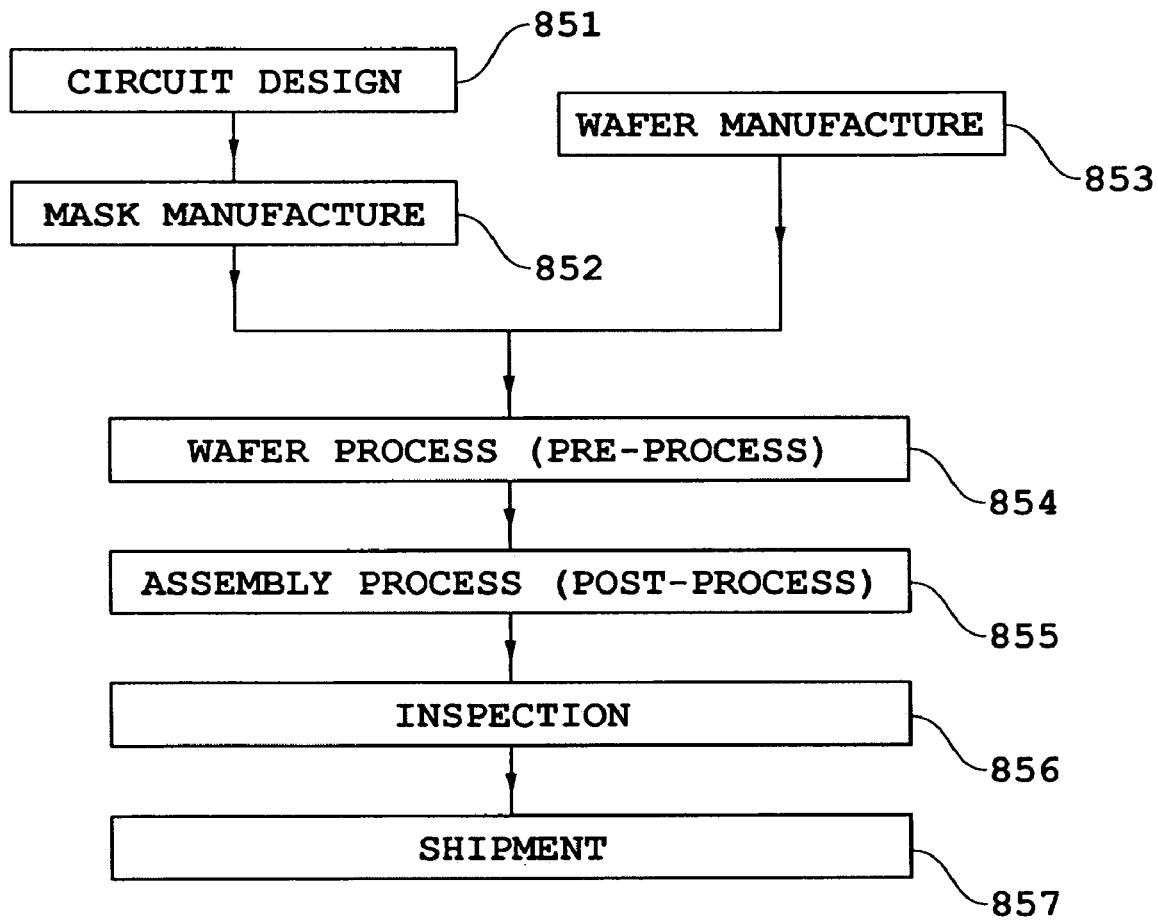
FIG. 3b is a flow chart of the sequence of manufacturing steps of a semiconductor device

As is well known in the art, lithography is a critical part of manufacturing methods for making semiconducting devices. For example, U.S. Pat. No. 5,483,343 outlines steps for such manufacturing methods. These steps are described below with reference to FIGS. 3b and 3c. FIG. 3b is a flow chart of the sequence of manufacturing a semiconductor device such as a semiconductor chip (e.g. IC or LSI), a liquid crystal panel or a CCD. Step 851 is a design process for designing the circuit of a semiconductor device. Step 852 is a process for manufacturing a mask on the basis of the circuit pattern design. Step 853 is a process for manufacturing a wafer by using a material such as silicon.

Step 854 is a wafer process, which is called a pre-process wherein, by using the so prepared mask and wafer, circuits are formed on the wafer through lithography. To form circuits on the wafer that correspond with sufficient spatial resolution those patterns on the mask, interferometric positioning of the lithography tool relative the wafer is necessary. The catoptric imaging systems described herein can be especially useful to inspect the surface of the wafer and internal layers generate on the wafer by wafer processing to check and monitor the effectiveness of the lithography used in the wafer process. Step 855 is an assembling step, which is called a post-process wherein the wafer processed by step 854 is formed into semiconductor chips. This step includes assembling (dicing and bonding) and packaging (chip sealing). Step 856 is an inspection step wherein operability check, durability check and so on of the semiconductor devices produced by step 855 are carried out. With these processes, semiconductor devices are finished and they are shipped (step 857).

Figure 3C:
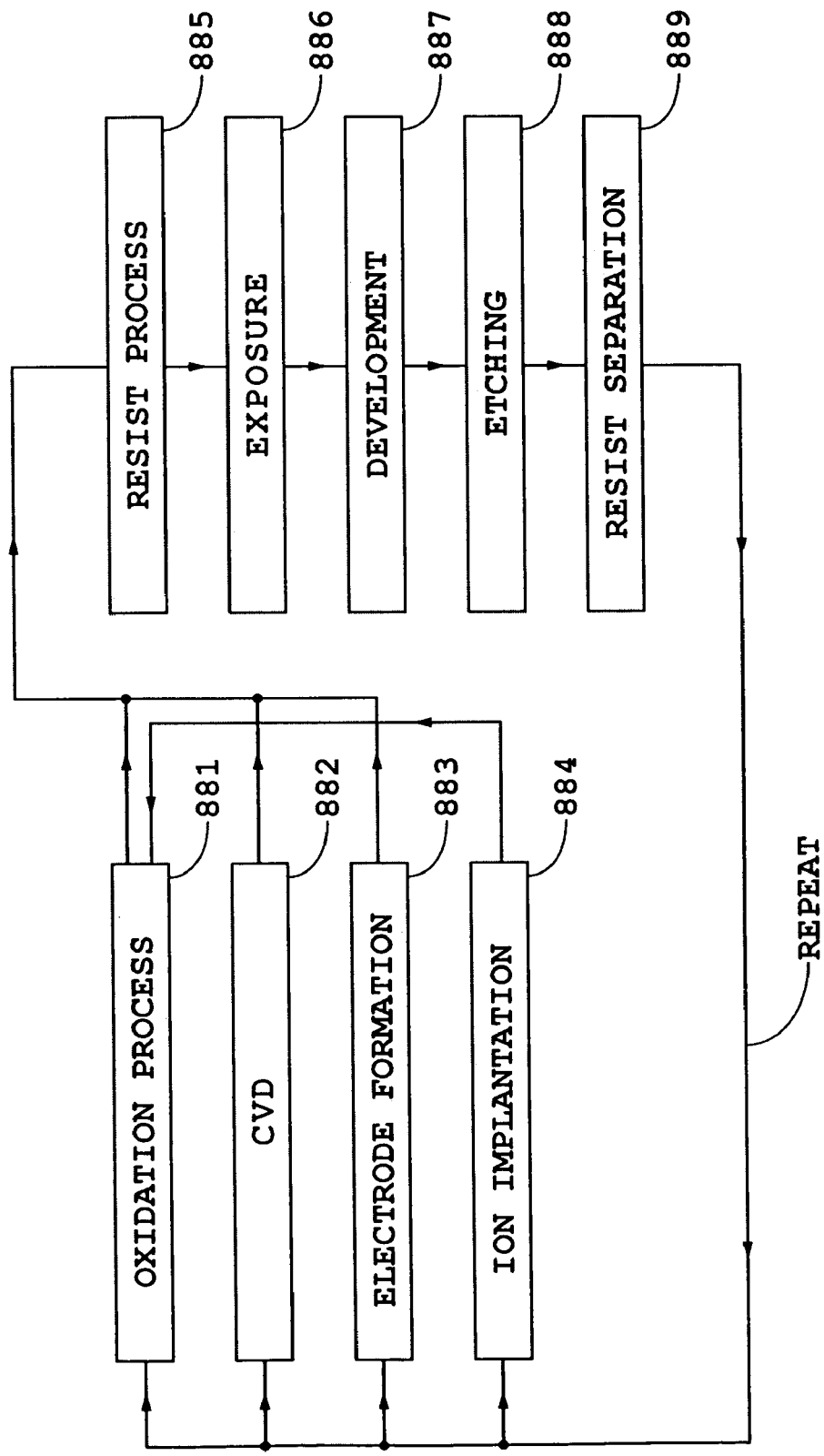
FIG. 3c is a flow chart showing steps of the wafer process.

FIG. 3c is a flow chart showing details of the wafer process. Step 861 is an oxidation process for oxidizing the surface of a wafer. Step 862 is a CVD process for forming an insulating film on the wafer surface. Step 863 is an electrode forming process for forming electrodes on the wafer by vapor deposition. Step 864 is an ion implanting process for implanting ions to the wafer. Step 865 is a resist process for applying a resist (photosensitive material) to the wafer. Step 866 is an exposure process for printing, by exposure (i.e., lithography), the circuit pattern of the mask on the wafer through the exposure apparatus described above. Once again, as described above, the use of the catoptric imaging systems described herein improve the accuracy, resolution, and maintenance of such lithography steps.

Step 867 is a developing process for developing the exposed wafer. Step 868 is an etching process for removing portions other than the developed resist image. Step 869 is a resist separation process for separating the resist material remaining on the wafer after being subjected to the etching process. By repeating these processes, circuit patterns are formed and superimposed on the wafer.

Figure 4:
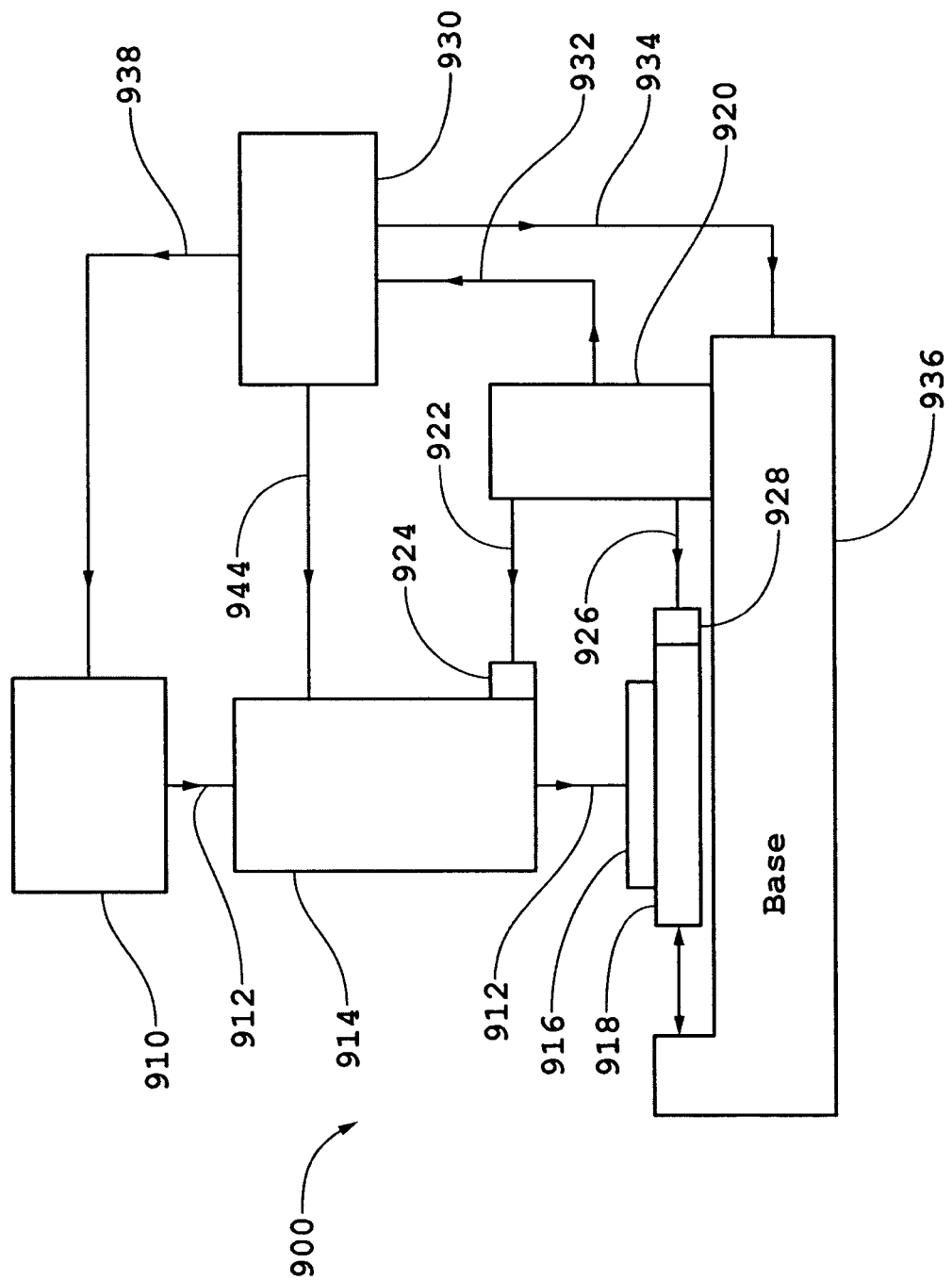
FIG. 4 is a schematic diagram of an inspection tool that uses catoptric imaging systems with pellicle or aperture array beam-splitters (not shown in figure).

An important application of the catoptric imaging systems described herein is the inspection of masks and reticles used in the lithography methods described previously. As an example, a schematic of a mask inspection system 900 is shown in FIG. 4. A source 910 generates a source beam 912 and a catoptric imaging system assembly 914 directs the radiation beam to a substrate 916 supported by a movable stage 918. To determine the relative position of the stage, an interferometry system 920 directs a reference beam 922 to a mirror 924 mounted on beam focusing assembly 914 and a measurement beam 926 to a mirror 928 mounted on stage 918. Changes in the position measured by the interferometry system correspond to changes in the relative position of write beam 912 on substrate 916. Interferometry system 920 sends a measurement signal 932 to controller 930 that is indicative of the relative position of inspection beam 912 on substrate 916. Controller 930 sends an output signal 934 to a base 936 that supports and positions stage 918.

Controller 930 can cause catoptric imaging system assembly 914 to scan the inspection beam over a region of the substrate, e.g., using signal 944. As a result, controller 930 directs the other components of the system to inspect the substrate. The mask inspection compares the mask pattern directly with computer data used to generate the mask.

While various embodiments of the invention has been described with reference to particular embodiments thereof, those skilled in the art will be able to make the various modifications to the described embodiments without departing from the true spirit and scope of the present invention.

Other embodiments are within the following claims.

What is claimed is:

1. An interferometry system comprising:
   a first imaging system that directs a measurement beam at an object to produce a return measurement beam from the object, that directs the return measurement beam onto an image plane, and that delivers a reference beam to the image plane; and
   a beam combining element in the image plane, said beam combining element comprising a first layer containing an array of sagittal slits and a second layer containing an array of tangential slits, wherein each slit of the array of sagittal slits is aligned with a corresponding different slit of the array of tangential slits, wherein the beam combining element combines the return measurement beam with the reference beam to produce an array of interference beams.

2. The interferometry system of claim 1, further comprising:
   a detector array; and
   a second imaging system that directs the array of interference beams from the beam combining element onto the detector array.

3. The interferometry system of claim 2, wherein the measurement beam is characterized by a wavelength $\lambda$, the first layer is made of a first absorbing material that absorbs at wavelength $\lambda$, and the second layer is made of a second absorbing material that absorbs at wavelength $\lambda$.

4. The interferometry system of claim 3, wherein the first and second absorbing materials are the same.

5. The interferometry system of claim 2, wherein the first layer is a planar-shaped layer and wherein the second layer is a concave-shaped layer.

6. The interferometry system of claim 2, wherein the beam combining element further comprises a third layer sandwiched between the first and second layers.

7. The interferometry system of claim 6, wherein the third layer is transmissive at wavelength $\lambda$.

8. The interferometry system of claim 6, wherein the third layer is absorbing at wavelength $\lambda$ and it includes an array of apertures each of which is aligned with a corresponding different one of the slits of the sagittal array of slits.

9. The interferometry system of claim 2, wherein the first imaging system is characterized by a sagittal imaging surface and a tangential imaging surface and wherein the first layer conforms to the sagittal imaging surface and the second layer conforms to the tangential imaging surface.

10. The interferometry system of claim 2, wherein the first imaging system is a catoptric imaging system.

11. The interferometry system of claim 2, wherein the first imaging system is characterized by an optical axis and the slits of the sagittal array of slits are aligned along radial directions relative to the optical axis.

12. The interferometry system of claim 2, wherein the first imaging system is characterized by an optical axis and the slits of the tangential array of slits are aligned along azimuthal directions relative to the optical axis.

13. The interferometry system of claim 11 wherein the lengths of the slits of the sagittal array of slits increase as a function of the distance of the slit from the optical axis.

14. The interferometry system of claim 12, wherein the lengths of the slits of the tangential array of slits increase as a function of the distance of the slit from the optical axis.

15. The interferometry system of claim 2, wherein the slits of the sagittal array of slits are v-shaped grooves.

16. The interferometry system of claim 2, wherein the slits of the tangential array of slits are v-shaped grooves.

17. The interferometry system of claim 1, wherein the slits of the sagittal array of slits are filled with a fluorescent material.

18. The interferometry system of claim 17, wherein the fluorescent material comprises lumogen.

19. The interferometry system of claim 17, wherein the fluorescent material is sensitive to UV, VUV or EUV.

20. The interferometry system of claim 17, wherein the fluorescent material is responsive to radiation at a first wavelength and emits radiation at a second wavelength, wherein the first and second wavelengths are different.

21. The interferometry system of claim 20, wherein the second wavelength is longer than the first wavelength.

22. The interferometry system of claim 20, wherein the fluorescent material is responsive to radiation in the UV, VUV or EUV region and the second wavelength is in the visible region.

23. The interferometry system of claim 20, further comprising:
a detector array that is responsive to radiation at the second wavelength; and
a second imaging system that directs the array of interference beams from the beam combining element onto the detector array.

24. The interferometry system of claim 2, wherein the first imaging system comprises:
a beam splitter positioned to receive the return measurement beam from the object and separate the return measurement beam into a transmitted portion and a reflected portion; and
a reflecting surface positioned to receive one of the transmitted portion and the reflected portion from the beam splitter and focus that received portion onto the image plane via the beam splitter.

25. The interferometry system of claim 24, wherein the first imaging system comprises an array of independently positionable reflecting elements forming the reflecting surface.

26. The interferometry system of claim 24, wherein the reflecting surface is a Fresnel reflecting surface.

27. The interferometry system of claim 24, wherein the reflecting surface is positioned to receive the transmitted portion of the measurement beam and reflect the transmitted portion of the measurement beam back to the beam splitter, and wherein the beam splitter is positioned to reflect rays received from the reflecting surface toward the image plane.

28. The interferometry system of claim 2, further comprising a beam splitting element including a first layer containing an array of sagittal slits and a second layer containing an array of tangential slits, wherein each slit of the array of sagittal slits of the beam splitting element is aligned with a corresponding different slit of the array of tangential slits of the beam splitting element, wherein the beam splitting element receives a source beam and generates therefrom an array of measurement beam components, said array of measurement beam components making up the measurement beam.

29. An interferometry system comprising:
a first imaging system that directs a measurement beam at an object to produce a return measurement beam from the object, that directs the return measurement beam onto an image plane, and that delivers a reference beam to the image plane; and
a beam combining element in the image plane, said beam combining element comprising an array of apertures that are configured and arranged to combine the return measurement beam with the reference beam to produce an array of interference beams containing diffraction limited information.

30. An interferometry system comprising:
a beam splitting element comprising a first layer containing an array of sagittal slits and a second layer containing an array of tangential slits, wherein each slit of the array of sagittal slits is aligned with a corresponding different slit of the array of tangential slits, wherein the beam splitting element receives a source beam and generates therefrom an array of measurement beams;
an imaging system that directs the array of measurement beams at an object to produce an array of return measurement beams from the object, that directs the array of return measurement beams onto an image plane, and that delivers a reference beam to the image plane; and
a beam combining element in the image plane that combines the array of return measurement beams with the reference beam to produce an array of interference beams.

31. The interferometry system of claim 30, wherein the a beam combining element comprises a first layer containing an array of sagittal slits and a second layer containing an array of tangential slits, wherein each slit of the array of sagittal slits of the beam combining element is aligned with a corresponding different slit of the array of tangential slits of the beam combining element.

* * * * *